US008381587B2

(12) United States Patent
Kasama et al.

(10) Patent No.: US 8,381,587 B2
(45) Date of Patent: Feb. 26, 2013

(54) GAS SENSOR, GAS MEASURING SYSTEM USING THE GAS SENSOR, AND GAS DETECTION MODULE FOR THE GAS SENSOR

(75) Inventors: Yasuhiko Kasama, Sendai (JP); Kenji Omote, Sendai (JP); Kuniyoshi Yokoo, Sendai (JP); Yuzo Mizobuchi, Sendai (JP); Haruna Oizumi, Sendai (JP); Morihiko Saida, Sendai (JP); Hiroyuki Sagami, Sendai (JP); Kazuaki Mizokami, Yokohama (JP); Takeo Furukawa, Tokyo (JP)

(73) Assignee: Ideal Star Inc., Miyagi (JP)

( * ) Notice: Subject to any disclaimer, the term of this patent is extended or adjusted under 35 U.S.C. 154(b) by 524 days.

(21) Appl. No.: 12/599,268

(22) PCT Filed: May 8, 2008

(86) PCT No.: PCT/JP2008/058571
§ 371 (c)(1),
(2), (4) Date: Mar. 3, 2010

(87) PCT Pub. No.: WO2008/140024
PCT Pub. Date: Nov. 20, 2008

(65) Prior Publication Data
US 2010/0206049 A1 Aug. 19, 2010

(30) Foreign Application Priority Data
May 8, 2007 (JP) .................................. 2007-123983
Dec. 6, 2007 (JP) .................................. 2007-316222

(51) Int. Cl.
*G01N 27/22* (2006.01)
(52) U.S. Cl. ...................... 73/335.04; 73/31.06; 977/957
(58) Field of Classification Search ............... 73/335.04, 73/31.06; 257/253; 977/734, 957
See application file for complete search history.

(56) References Cited

U.S. PATENT DOCUMENTS

| | | | | |
|---|---|---|---|---|
| 4,276,128 A | * | 6/1981 | Nishino et al. ............. | 73/335.04 |
| 5,334,351 A | | 8/1994 | Heinze et al. | |
| 6,174,780 B1 | * | 1/2001 | Robinson ...................... | 438/396 |

(Continued)

FOREIGN PATENT DOCUMENTS

| | | |
|---|---|---|
| JP | 5203604 A | 8/1993 |
| JP | 7225206 A | 8/1995 |

(Continued)

OTHER PUBLICATIONS

Machine Translation of JP 2005-214788A—Detailed Description to English. Translation obtained at <http://www.ipdl.inpit.go.jp/homepg_e.ipdl> Translation date: May 22, 2012.*

(Continued)

*Primary Examiner* — Lisa Caputo
*Assistant Examiner* — Punam Roy
(74) *Attorney, Agent, or Firm* — The Webb Law Firm

(57) ABSTRACT

A gas sensor, which is extremely compact to be arranged for separated gas piping in semiconductor device manufacturing equipment, a gas measuring system using such gas sensor, and a gas detection module for the gas measuring system. The gas sensor has a gas detection device containing a dielectric semiconductor, the electric conductivity of the gas detection device varying in response to the degree of adsorption of gases to the gas detection device, a capacitive element connected in series to the gas detection device, and a pair of electrodes which are connected to electric terminals of an electric element comprising the gas detection device and the capacitive element, wherein the gas sensor is capable of detecting the degree of adsorption of gases to the gas detection device from an electrical response to a voltage which is applied to the electrodes and which periodically varies and reverses in polarity.

10 Claims, 11 Drawing Sheets

U.S. PATENT DOCUMENTS

| | | | |
|---|---|---|---|
| 6,455,916 B1* | 9/2002 | Robinson | 257/532 |
| 6,793,967 B1* | 9/2004 | Ata et al. | 427/249.1 |
| 6,816,357 B2* | 11/2004 | Takatani et al. | 361/523 |
| 6,984,265 B1* | 1/2006 | Raguse et al. | 117/73 |
| 2003/0226996 A1* | 12/2003 | Aramaki et al. | 252/62.3 Q |
| 2006/0260674 A1* | 11/2006 | Tran | 136/252 |
| 2008/0030352 A1* | 2/2008 | Shaw | 340/579 |
| 2009/0113992 A1* | 5/2009 | Hunter et al. | 73/31.06 |
| 2009/0230979 A1 | 9/2009 | Omote et al. | |

FOREIGN PATENT DOCUMENTS

| | | |
|---|---|---|
| JP | 7239314 A | 9/1995 |
| JP | 2546608 B2 | 8/1996 |
| JP | 1010068 A | 1/1998 |
| JP | 11190710 A | 7/1999 |
| JP | 2005114355 A | 4/2005 |
| JP | 2005214788 A | 8/2005 |
| JP | 2005241540 A | 9/2005 |
| JP | 2006112819 A | 4/2006 |
| WO | 2007029684 A1 | 3/2007 |

OTHER PUBLICATIONS

A. F. Hebard, C. B. Eom, Y. Iwasa, K. B. Lyons, G.A. Thomas, D. H. Rapkine, R. M. Flemming, R. C. Haddon, J. M. Phillips, J. H. Marshall, and R. H. Elick, "Charge transfer at aluminum-C60 interfaces in thin film multilayer structures," Physical Review B (Condensed Matter), vol. 50, No. 23, Dec. 15, 1994, pp. 17740-17743.*

K. H. Bhuiyan and T. Mieno, "Modification of dielectric properties of C60, C70, and C84 thin films by oxygen absorption," Thin Solid Films, 506-507 (2006) pp. 239-243.*

J. S. Su, Y. F. Chen, and K. C. Chiu, "Dielectric properties of fullerene films," Appl. Phys. Lett. 74, 439 (1999) pp. 439-441.*

B. Pevzner, A. F. Hebard, and M. S. Dresselhaus, "Role of molecular oxygen and other impurities in the electrical transport and dielectric properties of C60 films," Physical Review B (Condensed Matter), vol. 55, No. 24, Jun. 15, 1997, pp. 16439-16449.*

Kroto et al., "C60: Buckminsterfullerene", Nature, Nov. 14, 1985, pp. 162-163, vol. 318.

Kratschmer et al., "Solid C60: a new form of carbon", Nature, Sep. 27, 1990, pp. 354-358, vol. 347.

Kratschmer et al., "The infrared and ultraviolet absorption spectra of laboratory-produced carbon dust: evidence for the presence of the C60 molecule", Jul. 6, 1990, Chem. Phys. Ltrs., pp. 167-170, vol. 170, No. 2,3.

* cited by examiner (a)

(b)

(c)

(a)　　　(b)

GAS SENSOR, GAS MEASURING SYSTEM USING THE GAS SENSOR, AND GAS DETECTION MODULE FOR THE GAS SENSOR

BACKGROUND OF THE INVENTION

1. Field of the Invention

The present invention relates to a gas sensor, a gas measuring system using the gas sensor, and a gas detection module for the gas sensor. In particular, the present invention relates to an extremely compact gas sensor which can be attached to gas piping of equipment for manufacturing a semiconductor device by using a highly sensitive gas detection device employable in the semiconductor field, a gas measuring system using the gas sensor, and a gas detection module for the gas sensor.

2. Description of Related Art

Fullerenes are a series of spherical molecules consisting only of carbon atoms, which were discovered by Kroto, et al. in a mass spectrum of cluster beams formed by the laser abrasion of carbon (Kroto, H. W; Heath, J. R.; O'Brien, S. C.; Curl, R. F.; Smalley, R. E. Nature 1985, 318, 162).

In the 1990's, the existence of a fullerene as a third crystalline carbon material following diamond and graphite was revealed, and a method of mass producing fullerenes by arcing a carbon electrode was developed (Kratschmer, W.; Fostiropoulos, K.; Huffman, D. R. Chem. Phys. Lett. 1990, 170, 167, and Kratschmer, W.; Lamb, L. D.; Fostiropoulos, K.; Huffman, D. R. Nature 1990, 347, 354).

Since fullerenes were discovered, it has been pointed out that fullerenes have unique optical, electrical, chemical, and mechanical properties. Therefore, fullerenes have been considered for use of such as a highly-sensitive sensitizer, an n-type semiconductor, a scavenger of active oxygens, and a microbearing.

However, since a carbon nanotube (CNT), which is a carbon nanomaterial similar to a fullerene, was discovered in the middle of the 1990's, researchers' interest has been focused on this CNT. Therefore, the basic characteristics of fullerenes have not been understood yet, although more than 20 years have passed since fullerenes were discovered. Thus, further investigation is required.

There are many types of materials which are categorized as materials based on a fullerene, which may be referred to as fullerene-based materials, a detailed explanation of which will be given below. Examples of fullerene-based materials include an endohedral fullerene, a heterofullerene (a compound having a fullerene skeleton, with a portion of the carbon atoms forming the skeleton having been replaced by atoms other than carbon such as nitrogen), a norfullerene (a compound having a fullerene skeleton, with a portion of the carbon atoms forming the skeleton having been removed), fullerene derivatives, and fullerene polymers. Manufacturing methods of most of these materials have not been established yet, and hence properties of these materials have not been clarified.

One of the specific applications of a fullerene material, which is a generic name for fullerenes and fullerene-based materials, is a gas detection device for a gas sensor (see Patent Document 1, for example).

Patent Document 1 discloses a gas sensor using a material containing fullerenes, which enables to detect the oxygen content of at most $10^{14}$ atoms/cm$^3$ and the water content of at most $10^{16}$ atoms/cm$^3$. The initial conductance of the gas sensor disclosed in Patent Document 1 is 0.1 (ohm cm)$^{-1}$. When oxygen at atmospheric pressure is introduced to the gas sensor, the conductance falls to $2\times10^{-9}$ (ohm cm)$^{-1}$. When the gas sensor after the introduction of oxygen is heated in a nitrogen atmosphere so that the oxygen in the gas sensor is exhausted, the conductance returns to around 0.1 (ohm cm)$^{-1}$. Namely, Reference 1 discloses that the conductance of the material containing fullerenes reversibly changes.

Patent Document 1: WO2007/029684

SUMMARY OF THE INVENTION

A gas sensor using the above-described material has a high detection sensitivity. Therefore, it can be used for detecting contaminated gases in a semiconductor manufacturing line. However, because a gas sensor containing fullerenes is easily affected by manufacturing procedures and measurement conditions, it is not easy to guarantee high repeatability and high reliability for the gas sensor.

The object of the present invention is to provide an extremely compact gas sensor which can be attached to an individual gas pipe of equipment for manufacturing a semiconductor device by using a highly sensitive gas detection device employable in the field of semiconductor processing, and a gas measuring system using the gas sensor.

The present inventors hypothesized that a fullerene material could be a component of a gas detection device which resolves the above-described objective. Base on that hypothesis, the present inventors performed investigations for obtaining a sensor system in which the properties of the fullerene materials are fully exploited. The present inventors obtained the following knowledge through the investigation.

(a) It is well known that a member containing a fullerene material, such as a deposited film of a fullerene material, increases in resistance, namely, it decreases in electric conductivity when gaseous materials are adsorbed on the member. However, when the amount of adsorbed gases is sufficiently small, the electric conductivity of a member containing a fullerene material becomes as high as the electric conductivity of a highly conductive inorganic semiconductor.

(b) On the other hand, the member containing the fullerene material exhibits dielectric characteristics. Namely, the fullerene material can be defined as a dielectric semiconductor.

(c) When a DC voltage is applied to a gas sensor using a gas detection device containing such a dielectric semiconductor, the dielectric characteristics cause a destabilizing phenomenon such as a charging phenomenon. Therefore, it is preferable to apply an AC voltage when a dielectric semiconductor is used as a raw material of a highly sensitive sensor. Namely, the gas sensor exhibits excellent stability when an AC voltage is applied and an electrical response on susceptance such as capacitance is measured.

(d) When a capacitive element is electrically connected in series to the gas detection device and the real part of the complex capacitance of an electric element consisting of the dielectric semiconductor and the capacitive element is measured, the effect of noise during measurement is reduced. Therefore a gas sensor with excellent sensitivity can be obtained from the electric element.

(e) The detection capability of the gas sensor can be controlled by adjusting the capacitance of the connected capacitive element. Therefore, the difficulty of controlling the quality of the manufacturing process of the gas detection device containing the dielectric semiconductor is reduced. Accordingly, a highly sensitive gas sensor can be obtained with good productivity.

The present invention described below is provided a concept based on the above-described knowledge.

A gas sensor provided as one aspect of the present invention comprises a gas detection device containing a dielectric semiconductor, where the electric conductivity of the gas detection device varies corresponding to the degree of adsorption of gases to the gas detection device, a capacitive element being connected in series with the gas detection device, where the capacitance of the capacitive element is larger than the capacitance of the gas detection device, and a pair of electrodes which are connected to electric terminals of an electric element comprising the gas detection device and the capacitive element, wherein the gas sensor is capable of detecting the degree of adsorption of gases to the gas detection device from changing on an electrical response for an applied voltage which is applied to the pair of electrodes and which periodically varies and reverses in polarity.

"A dielectric semiconductor" is a semiconductor material having dielectric characteristics. When an external voltage is applied to a dielectric semiconductor, a charge polarization occurs in a dielectric semiconductor due to the electric field generated by the applied voltage, and a prescribed capacitance is measured because of the charge polarization. At the same time, electric charge carriers move in the dielectric semiconductor due to the external voltage, and a prescribed conductance is measured because of the charge transfer. Therefore, the equivalent circuit of the dielectric semiconductor consists of a resistive component and a capacitive component which is connected in parallel to the resistive component.

There is no limitation of the components on the dielectric semiconductor as long as it has the above-described properties. Examples of the dielectric semiconductor include organic semiconductors and carbon nanomaterials. Examples of carbon nanomaterials include fullerene materials and carbon nanotubes. When the gas to be adsorbed has high electron acceptability such as oxygen or water vapor, electroconductive properties of the dielectric semiconductor are preferably affected by the absorbed gases.

"An electrical terminal" is a part of an electric element where a voltage is applied and an electric response is measured so that the electric element can perform its function.

"The electric conductivity of the gas detection device varying in response to the degree of adsorption of gases on the gas detection device" means that the electric conductivity of the gas detection device varies due to a phenomenon that gases adsorbed to the gas detection device change in quality and/or amount. Examples of a change in quality include a change of species of the adsorbed gases, a change of the degree of the chemical interaction between the adsorbed gases and the materials constituting the gas detection device, and a change of the region of adsorbed gases in the gas detection device, such as a phenomenon that gases adsorbed on the surface of the gas detection device transfer to the inside of the gas detection device.

The adsorbed gases contain at least one species of gas which can change the electric conductivity of the gas detection device, and the adsorbed gases may contain gases which cannot change the electric conductivity of the gas detection device, which may be referred to as inert gases.

"A voltage which periodically varies and reverses in polarity" means a voltage having a prescribed wave profile, wherein the wave profile is repeatedly applied in a prescribed period, and when the voltage is applied to the electrodes, the potential difference between the electrodes varies from negative to positive due to the wave profile. The typical example of such a changing voltage is an AC voltage having a sinusoidal wave profile. The wave profile of the applied voltage is not limited to a sine curve. The wave profile may be a rectangular wave or a triangular wave. The center value of the applied voltage may be neutral, or shifted from a zero potential.

"An electric response" means an electrically-measurable response of the gas sensor to an applied voltage which periodically varies and reverses in polarity. Therefore, there is no limitation on electric parameters for measuring the electric response. A change of current may be measured. Impedance or admittance, which is the inverse of impedance, may be measured. Complex conductance may be measured. It is preferable that an AC voltage be applied and that complex conductance be measured.

"A capacitive element" is an electric element having dielectric properties and the capacitive element is different from the capacitive component of the dielectric semiconductor contained in the gas detection device. A prescribed capacitance is measured when a voltage is applied to electrical terminals of the capacitive element. The shape of the capacitive element is not limited. The capacitive element may be in the form of a capacitive element which is a commercially-available electric part. The capacitive element may be in the form of a film, a block, or a line, which has a structure that a layer consisting of a dielectric material is sandwiched between two layers consisting of an electric conductive material. The capacitive element may consist of a dipole such as an electric double layer or an electric barrier. It is advantageous that the gas sensor have a structure such that at least a part of the capacitive element directly contacts the gas detection device so that the gas sensor can be small in size.

"An electric element comprising the gas detection device and the capacitive element" means an electric element in which the gas detection device and the capacitive element are connected in series. The electric element may further contain a resistive element such as a wiring resistance. A resistive element may be connected in parallel with the capacitive element contained in the electric element.

Any electric parameter may be employed for measuring an electric response of the above-described gas sensor. It is preferable that an AC voltage be applied and that the real part of the complex capacitance (this parameter may be referred to as "a real part of capacitance" or "a capacitance".) or the conductance be measured.

The capacitance of the capacitive element of the above-described gas sensor is preferably larger than the capacitance of the gas detection device.

The electric conductivity of the gas detection device can be measured with high sensitivity by measuring the dependency of the real part of the complex capacitance on the frequency of the applied voltage which is measured, when the capacitance of the capacitive element is set to be larger than the capacitance of the gas detection device. The measurement of the electric conductivity can be stably performed when the ratio of the capacitance of the capacitive element to the capacitance of the gas detection device is at least 10. The measurement can be quantitatively performed when the ratio is at least 100.

The gas sensor may be composed of a plurality of members.

The above-described "member" may be an individual part such as a commercially available capacitor, or a region having dielectric properties, the region having an structure and being formed on a substrate, on which the gas detection device is also formed.

The above gas sensor may comprise a metal layer formed directly on the surface of an electric terminal of the gas detection device. In this case, the metal layer has a modified dielectric layer obtained by modifying a metal of the metal layer at the interface facing the gas detection device, and the modified dielectric layer is at least a part of the capacitive element.

The modified dielectric layer may be formed by oxidizing the metal positioned at the interface facing the gas detection device of the metal layer. The modified dielectric layer may be a nitride or carbide of the metal. The modified dielectric layer may be a complex of the above-described materials such as a carbonitride. The capacitive element may comprise not only the modified dielectric layer but also a dipole and/or an electric barrier which are formed near the interface between the modified dielectric layer and the gas detection layer.

The modified dielectric layer of the gas sensor may be an oxide film formed by the oxidation of the metal of the metal layer with oxygen passing through the gas detection device.

The oxide film may be a natural oxide film which is formed by spontaneously oxidizing the surface of the metal layer in the ambient atmosphere. The oxide film may be an oxide film which is formed by actively oxidizing the surface of the metal layer, such as by heating the surface of the metal layer in an atmosphere containing oxygen. From the viewpoint of effectively forming a natural oxide film, examples of preferable metals include aluminum, titanium, chromium, nickel, niobium, and tantalum.

The above-described gas sensor may comprise a dielectric material layer formed directly on the surface of an electric terminal of the gas detection device, and the dielectric material layer is at least a part of the capacitive element and prevents charge injection to the gas detection device.

Examples of a raw material of the dielectric material layer include an oxide, which preferably has a high permittivity. A specific example of such an oxide is a $HfO_2$-type material. It is preferable that the thickness of the dielectric material layer be at least 1 nm so as to prevent charge injection caused by tunneling.

The above-described gas sensor may comprise a pair of inert metal layers respectively formed directly on the surface of electric terminals of the gas detection device, and a gas detection module, which consists of the gas detection device and the pair of inert metal layers sandwiching the gas detection device. The gas detection module does not substantially contain an electric element which has dielectric characteristics other than the gas detection device.

The inert metal is defined as a metal like gold which does not substantially form a natural oxide layer.

The above-described dielectric semiconductor may consist of a fullerene material having properties that its electric conductivity is decreased by the adsorption of a gas.

As explained above, the term "fullerene material" is a generic name for fullerenes and fullerene-based materials. A fullerene is a hollow cluster of carbon atoms, and term "fullerene-based material" is a generic name for a compound synthesized from a fullerene and a compound having a basic structure which is similar to the structure of a fullerene.

Examples of a gas detection device consisting of a fullerene material include a single crystal obtained by sublimating a fullerene material, a deposited film obtained by sublimating a fullerene material, an epitaxial film obtained by depositing molecular beams of a fullerene material, and a film obtained by coating a fullerene material dissolved in appropriate solvent and eliminating the solvent of the coated film by heating at a temperature more than 200 degrees C. in vacuum.

When the gas detection device is in the form of a film, the film is preferably formed on a dielectric substrate such as a ceramic, and the permittivity of the dielectric substrate is preferably low.

There is no limitation on the form of the gas detection device. It may be a film, a block, or a line.

The above-described dielectric semiconductor may comprise an organic semiconductor.

An organic semiconductor is an organic material having semiconductor characteristics, and the gas detection device preferably contains one or more materials selected from the group consisting of phthalocyanine, pentacene, anthracene, $Alq_3$, thiophene, aniline, polyaniline, polythiophene, and polyparaphenylenevinylene.

The above-described dielectric semiconductor may comprise a carbon nanomaterial.

A carbon nanomaterial is a compound mainly consisting of carbon and having a nanoscale basic structure. A fullerene material is one carbon nanomaterial. The gas detection device preferably contains one or more materials selected from the group consisting of fullerenes, endohedral fullerenes, heterofullerenes, carbon nanotubes, carbon peapods, carbon nanoonions, derivatives of the above-described compounds, and polymers of the above-described compounds and derivatives.

A gas sensor provided as another aspect of the present invention comprises the above-described gas sensor, an electric power supply capable of applying a voltage to electric terminals of the gas sensor, wherein the applied voltage periodically varies and reverses in polarity, and a measuring means for measuring an electric response of the gas sensor to the voltage applied by the electric power supply.

The electric power supply is preferably capable of changing the frequency of the periodically varying voltage and is further preferably capable of a voltage signal in which a plural of varying voltages having different frequencies from each other are superimposed. All or part of the capacitive element may be integrated with the electric power source. The measuring means may be integrated with the electric power source and/or the capacitive element. The measuring means may contain a means for calculating the change of the electric conductivity of the gas detection device based on the measured electric response and a means for calculating the change of the amount of adsorbed gases.

The above-described gas measuring system may further comprise a gas desorbing means for desorbing a gas adsorbed by the dielectric semiconductor contained in the gas sensor.

Specific examples of the gas desorbing means include means for heating with a heater, means for irradiation with a infrared light, means for irradiation with a laser, means for irradiation with high-energy particles, and means for reducing the partial pressure of the desorbed gas in the ambient atmosphere of the gas detection device, such as exhaust equipment or gas supply equipment supplying high-purity inert gases. The gas desorbing means may be integrated with the gas detection device. For example, the gas desorbing means may be composed of a ceramic heater and the gas detection device may be in the form of a film formed on the ceramic heater.

The above-described gas measuring system may further comprise a temperature measuring means for measuring the temperature of the gas sensor. The structure of the temperature measuring means may be the same as that of the gas sensor except that the temperature measuring means is sealed so that no gas is adsorbed in the temperature measuring means of a gas detection device.

The structure of the temperature measuring means need not to be completely identical to the structure of the gas detection device. The structure of the temperature measuring means is substantially the same as the structure of the gas detection device when the change of the electric conductivity in response to the change in temperature of the temperature measuring means is substantially the same as that of the gas sensor, and hence the effect of the change of the electric conductivity due to the change in temperature of the gas sensor can be reduced and the change of the electric conductivity due to the adsorption of gases can be calculated by a proper calculation based on the change of the electric conductivity of the gas sensor and the change of the electric conductivity of the temperature measuring means.

A gas detection module for the above-described gas measuring system is provided as yet another aspect of the present invention. The gas detection module consists of the above-described gas detection device, and a pair of inert metal layers respectively formed directly on the surface of electric terminals of the gas detection device. The gas detection module does not substantially contain an electric element which has dielectric characteristics other than the gas detection device.

A method of measuring gases is also provided as yet another aspect of the present invention. The method uses a gas measuring system comprising the above-described gas sensor, an electric power supply capable of applying a voltage to electric terminals of the gas sensor, the applied voltage periodically varying and reversing in polarity, and a measuring means for measuring an electric response of the gas sensor to the voltage applied by the electric power supply. The dependence of the real part of the complex capacitance of the gas sensor on the frequency of the applied voltage has a profile which consists of a first zone at a higher frequency, a second zone at a lower frequency, and a third zone between the first zone and the second zone, the value of the first zone being defined mainly by the capacitance of the gas detection device of the gas sensor, and the value of the second zone being defined mainly by the capacitance of the gas detection device. The degree of adsorption of gases to the gas sensor is detected by measuring at least one of the value of the second zone and the value of the third zone of the profile.

The real part of the complex capacitance in the first zone almost corresponds to the capacitance of the gas detection device of the gas sensor. The value of the real part of the complex capacitance in the third zone is similar to the value of the capacitance of the capacitance element of the gas sensor. Therefore, the value of the real part of the complex capacitance in the third zone widely changes from the value in the first zone to the value in the third zone, and hence the second zone forms a transition zone.

When the gas sensor has a structure in which the resistance of a resistive element which is electrically connected in parallel with the capacitive element cannot be regarded as infinite, the value of the real part of the complex capacitance in the second zone varies in accordance with the resistance of the resistive element.

Since the gas sensor according to the present invention has a structure in which the gas detection device and the capacitive element are connected in series, the electric response to an applied voltage which periodically varies and reverses in polarity happened effectively by absorption of gasses. Therefore, high sensitive detection in the change of the electric conductivity of the gas detection device becomes possible. In particular, much more sensitive detection of gases is achieved by measuring the real part of the complex capacitance of the gas sensor or the conductance of the gas sensor as an electric parameter for detecting the electric response and analyzing the profile data obtained by measuring the dependence of the electric parameter on the applied frequency. Furthermore, when the gas sensor has a structure in which part of the capacitive element is formed so as to be unified with the gas detection device, the difficulty of quality control when manufacturing the gas sensor is reduced, and hence reliable manufacture of gas sensors with high quality is achieved.

DETAILED DESCRIPTION OF THE PREFERRED EMBODIMENTS

Figure 1:
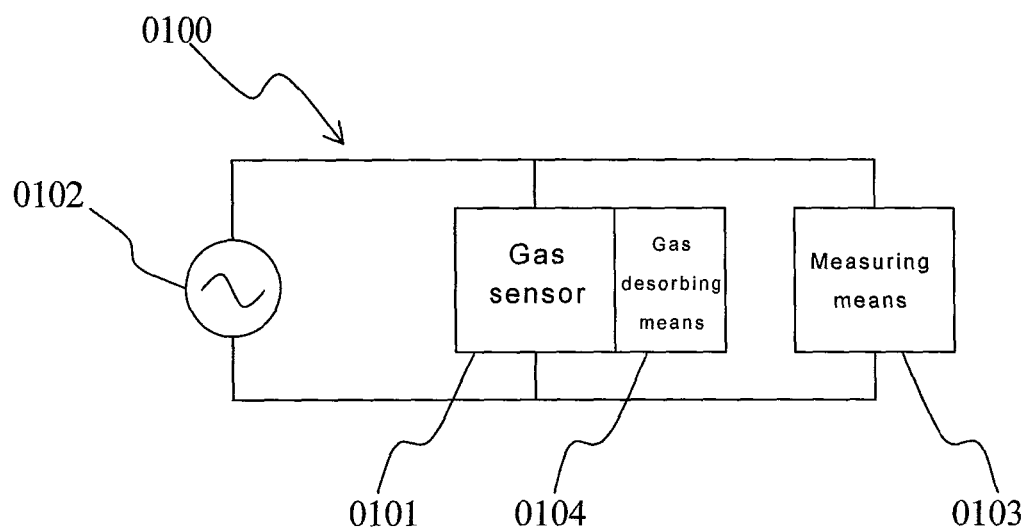
FIG. 1 is a schematic diagram showing a gas measuring system according to a first embodiment of the present invention.

Although typical embodiments of the present invention will be explained below, the present invention is not limited to the described embodiments. Therefore, any variations of the embodiments are to be considered as being within the scope of the present invention.

1. Dielectric Semiconductor (1) Definition

A dielectric material is a substance which generates dielectric polarization without a direct current in an electric field (Kenji Uchino, "Ferroelectric Device", 2005). Therefore, dielectric characteristics are defined as properties which generate dielectric polarization without a direct current in an electric field.

A semiconductor is a material which generates electric conductivity by the formation of a carrier which enables charge transfer in the conduction band or in the valence band because of reasons such as transfer of an electron from the valence band to the conduction band through the forbidden band.

Therefore, a semiconductor having dielectric characteristics, which may be referred as to a dielectric semiconductor, is defined as a material in which, when a voltage is applied to the material, dipole polarization is generated in the material due to the electric field caused by the applied voltage and a carrier of charge moves due to the applied voltage.

Examples of dielectric polarization include electronic polarization, ionic polarization, orientational polarization, and space-charge polarization. Any type of polarization can be involved in a dielectric semiconductor. The carrier of a charge may be an electron or a hole. A dielectric semiconductor may be doped with an atom and/or a molecule so as to generate a carrier and to modify the electric conductivity of the dielectric semiconductor.

Since a dielectric semiconductor has the above-described characteristics, the equivalent circuit of a dielectric semiconductor consists of a capacitive component and a resistive component connected to the capacitive component in parallel.

(2) Organic Semiconductor

Examples of a dielectric semiconductor include an organic semiconductor and a carbon nanomaterial.

An organic semiconductor is an organic substance having characteristics as a semiconductor. Examples of an organic semiconductor include perylenetetracarboxylic dianhydride and its derivatives, derivatives of perylenetetracarboxydiimide, naphthalenetetracarboxylic dianhydride and its derivatives, derivatives of naphthalenetetracarboxydiimide, derivatives of phthalocyanine, and a coordination compound having a quinoline skeleton or a benzoquinoline skeleton such as tris-(8-hydroxyquinoline)aluminum ($Alq_3$), tris-(4-methyl-8-hydroxyquinoline)aluminum ($Almq_3$), bis(10-hydroxybenzo[h]-quinolinato)beryllium ($Bebq_2$), and bis(2-methyl-8-quinolinolato)(4-phenylphenolato)aluminum (BAlq).

The examples also include an oxazole-type coordination compound such as bis(2-(2-hydroxyphenyl)benzoxazolate) zinc ($Zn(BOX)_2$) and a thiazole-type coordination compound such as bis(2-(2-hydroxyphenyl)benzothiazolate)zinc ($Zn(BTZ)_2$). The examples further include a compound which is not a coordination compound such as 2-(4-biphenylyl)-5-(4-tert-buthylphenyl)-1,3,4-oxadiazole (PBD), 1,3-bis[(p-tert-butyl)phenyl-1,3,4-oxadiazoyl]benzene (OXD-7), 3-(4-biphenylyl)-4-phenyl-5-(4-tert-butylphenyl)-1,2,4-triazole (TAZ), 3-(biphenyl-4-yl)-5-(4-dimethylaminphenyl)-4-(4-ethylphenyl)-1,2,4-triazole (p-EtTAZ), bathophenanthroline (Bphen), bathocuproine (BCP), and their derivatives, the main chain of which consists of a molecular skeleton formed by the combination of the above-described compounds.

An organic semiconductor preferably comprises one or more compounds selected from the group consisting of phthalocyanine, pentacene, anthracene, $Alq_3$, thiophene, aniline, polyaniline, polythiophene, and polyparaphenylenevinylene.

(3) Carbon Nanomaterial

A carbon nanomaterial is a compound mainly consisting of carbon and having a nanoscale basic structure. Examples of a carbon nanomaterial include, in addition to the fullerene materials described below, carbon nanotubes, carbon peapods, carbon nano-onions, derivatives of the above-described compounds, and polymers of the above-described compounds and derivatives.

(4) Fullerene Material

As described above, the term "fullerene material" is a generic name for fullerenes and fullerene-based materials. It is one of the most typical dielectric semiconductors.

A fullerene is a hollow cluster of carbon atoms having an almost-spherical shape. The chemical formula of a fullerene is $C_n$ (n=60, 70, 76, 78, etc). A fullerene has a structure containing twelve pentagonal carbon rings and at least twenty hexagonal carbon rings. Specific examples of fullerenes include $C_{60}$ and $C_{70}$.

A fullerene-based material is a compound synthesized from a fullerene or a compound having a basic structure similar to the structure of a fullerene. Examples of a fullerene-based material include the following materials.

An endohedral fullerene is basically a compound having a fullerene skeleton in the carbon hollow cage of which one or more atoms other than carbon, or one or more molecules are capsulated. An atom or molecule to be captured in a fullerene molecule (cage) is referred as to an object atom (or molecule) of an endohedral fullerene, and an atom or molecule which is captured is referred as to a captured atom (or molecule). Examples of an object atom theoretically include all elements defined in the periodic table. Specific examples of an object atom include alkali metals such as Li, Na, and K, lanthanide metals such as La and Ce, and representative elements such as B, N, F, and Cl. There is no limitation on an object molecule. Examples of an object molecule include $H_2$, $N_2$, and $A_{3-x}B_xN$, where X is an integer between 1 to 3, A and B represent metals. An example of a typical compound having the formula $A_{3-x}B_xN$ is $Sc_3N$.

A heterofullerene is a compound having a fullerene skeleton in which a part of the carbon atoms constructing the skeleton are replaced with other atoms such as nitrogen. There is no limitation on its structure as long as the number of substituted atoms is at least one.

A norfullerene is a compound having a fullerene skeleton and a part of carbon atoms constructing the skeleton are removed. Carbon atoms left in the fullerene skeleton after the removal of carbon atoms may be terminated by hydrogen atoms. Although there is no limitation on the number of removed carbon atoms, the number is normally at most 5 so as to maintain the fullerene skeleton.

A secofullerene is a compound in which there is at least one cleavage of a carbon-carbon bond in the fullerene skeleton and carbon atoms at the cleavage are terminated by atoms such as hydrogen. Although there is no limitation on the number of the cleavages, the number is normally at most 10 so as to maintain the fullerene skeleton.

A derivative of a fullerene is a compound in which at least one atom or at least one residual molecule is bonded to at least one carbon atom composing the fullerene skeleton. Typical examples of a compound to which at least one atom is bonded include hydrogenated fullerenes, oxidized fullerenes, and halogenated fullerenes. Typical examples of a compound to which at least one residue is bonded include PCBM (phenyl $C_{61}$-butyric acid methyl ester) and hydroxylated fullerenes.

A fullerene polymer is obtained by chemical bonding between the same species or different species of fullerenes and the above-described fullerene-based materials.

A fullerene mixture is a mixture of fullerenes and the above-described fullerene-based materials.

2. Gas Detection Device (1) Composition

The gas detection device of the present invention contains the above-described dielectric semiconductor. The electric conductivity of the gas detection device varies in response to the degree of adsorption of gases to the gas detection device based on the properties of the dielectric semiconductor. Typically, the electric conductivity of the dielectric semiconductor varies as a result of adsorption of gases. Examples of changes in the electric conductivity corresponding to the degree of adsorption of gases include qualitative and quantitative changes of adsorbed gases in the dielectric semiconductor. Examples of qualitative changes include changes in gas species, that is, exchange in absorbed gas species, changes in the degree of interaction between gases and a material constituting the gas detection device such as a transition from physical adsorption to chemical adsorption, and changes in the location of adsorbed gases in the gas detection device such as a transition from adsorption at the surface of the gas detection device to adsorption inside the gas detection device caused by diffusion of the gases in the gas detection device.

The phenomenon of adsorption will be explained in more detail by taking a single crystal of $C_{60}$ fullerene as an example. A single crystal of $C_{60}$ fullerene has a molecular density of $1.44 \times 10^{21}$ molecules/cm$^3$. When this single crystal is exposed to the ambient atmosphere at room temperature at 50% RH, water is adsorbed on the single crystal. The molecular density of the adsorbed water in the saturated condition was measured by the present inventors to be about $2 \times 10^{20}$ molecules/cm$^3$. Therefore, it is estimated that the ratio of the number of $C_{60}$ fullerene molecules forming the single crystal to the number of adsorbed water molecules is 7.6. In the above-described condition, oxygen is also adsorbed on the single crystal. The molecular density of the adsorbed oxygen was measured to be about $2 \times 10^{18}$ molecules/cm$^3$. Therefore, it is estimated that the ratio of the number of $C_{60}$ fullerene molecules forming the single crystal to the number of adsorbed oxygen molecules is 860. It was clarified by these measurements that adsorbed molecules are adsorbed not only on the molecules forming the surface of the single crystal of $C_{60}$ fullerene but also on the molecules inside of the single crystal in the saturated condition.

As explained above, a huge number of molecules can be adsorbed to a single crystal of $C_{60}$ fullerene, and a deposited film of $C_{60}$ fullerene has similar adsorption properties to a single crystal. Therefore, a gas detection device consisting of a deposited film of $C_{60}$ fullerene changes in electric conductivity by as much as $10^8$ times.

Fullerene materials other than $C_{60}$ fullerene show a similar behavior to that of $C_{60}$ fullerene, but the degree of change in electric conductivity varies depending on the type of fullerene material, the chemical structure of the fullerene material forming the gas detection device such as the bonding structure with other fullerene materials, and the species of gases adsorbed to the gas detection device.

The sensitivity to oxygen of a gas detection device consisting of $C_{60}$ fullerene and an endohedral alkali metal fullerene such as Li@$C_{60}$ is higher than the sensitivity of a gas detection device consisting only of $C_{60}$ because the electric conductivity of a gas detection device containing endohedral alkali metal fullerene is higher than that of a gas detection device consisting only of $C_{60}$, and hence a larger current is obtained from a gas detection device containing endohedral alkali metal fullerene under the same measurement conditions. Therefore, the size of a device containing endohedral alkali metal fullerene can be smaller than the size of a device consisting only of $C_{60}$ fullerene when the measuring current is fixed to be same for both devices.

The electric conductivity of carbon nanomaterials other than a fullerene material also varies (normally decreases) due to the adsorption of gases.

A gas detection device containing an organic semiconductor as a dielectric semiconductor may increase in electric conductivity by the adsorption of gases, since electric conductivity of the gas detection device becomes higher by absorption of gases when electrodonating organic semiconductor is used as gas detection layer.

The gas detection device of the present invention may contain any material as long as the gas detection device contains a dielectric semiconductor which changes in the electric conductivity by absorption of gases. The gas detection device may contain an insulator such as a ceramic, an electric conductive material such as a metal, or a material having intermediate properties between those of an insulator and an electric conductive material.

(2) Structure

There is no further limitation on the structure of the gas detection device as long as the gas detection device has a structure which comprises a dielectric semiconductor, and a pair of electric terminals to which a voltage which periodically varies and reverses in polarity is applied via electrodes electrically contacting to the electric terminals, and gases to be measured can be adsorbed on the dielectric semiconductor disposed between the pair of electric terminals. One typical example of an applied voltage is an AC voltage centered around 0V.

The gas detection device may have the shape of a film, a block, or a line.

There is no limitation on a means for supporting the gas detection device. When the gas detection device has the shape of a film, the gas detection device is preferably formed on a supporting member which is composed of an insulator which preferably has a lower permittivity than the gas detection device. No supporting member is required when the gas detection device is in the form of a block or a line.

(3) Method of Manufacturing the Gas Detection Device

There is no limitation on a method of manufacturing the gas detection device as long as the device functions as a dielectric semiconductor.

One example of a method of manufacturing a gas detection device consisting of a fullerene material will be explained below.

One preferred method is to sublimate the fullerene material by heat. A gas detection device consisting of a single crystal or a deposited film obtained by sublimation has superior properties. The specific means for heating and the heating temperature can be selected based on the fullerene material to be heated. Examples of specific means for heating include resistive heating, heating with an electron beam, and heating with a laser.

When a material such as copper phthalocyanine, which has a comparable sublimation temperature with that of the fullerene material, is sublimated simultaneously by providing in a pot with the fullerene material, a deposited film having a certain content of both the material is obtained. The impurity content of this deposited film can be extremely low because the impurity content can be reduced as low as possible by purification of deposited material through sublimation process.

An MBE film is obtained by epitaxial growth of a fullerene material which is produced by supplying molecular beams of the fullerene material. The crystal structure of an MBE film is comparable to that of the crystal structure of a single crystal. Therefore, a gas detection device consisting of this MBE film also has superior properties.

The gas detection device may consist of a sputtered film produced by sputtering the fullerene material under an inert gas atmosphere such as argon. In this process, the fullerene material is not heated. The impurity content of a sputtered film is a bit of higher than that of a deposited film, since a sputtered film may contain a byproduct of the fullerene material or a gas in the atmosphere. However, a sputtered film has the advantage to produce the gas detection device with high productivity.

The gas detection device may be produced by introducing a sublimated fullerene material into a plasma to form a polymer of the fullerene material and depositing the polymer in the shape of a film. This deposited film also inevitably contains a small amount of impurities.

In addition to the above-described dry processes, the detection device may be manufactured by preparing a solution or a dispersion of a fullerene material by dissolving or dispersing the fullerene material in a proper medium, forming a thin-layer coating of the solution or dispersion by proper means such as spincoating, and vaporizing the medium from the coating layer. When this method is employed, the gas detection device can be manufactured without expensive vacuum equipment.

The gas detection device may be manufactured as a pellet obtained by compressing a fullerene material in the form of a powder. A dense gas detection device can be easily obtained by deaeration during the compressing process with a vacuum pump.

The gas detection device manufactured by the above-described processes may be irradiated with light, electrons, or the like, so as to polymerize all or part of the fullerene material contained in the gas detection device. The heat resistance of the gas detection device is improved by the polymerization.

3. First Embodiment (1) Composition

FIG. 1 is a diagram which schematically illustrates a gas measuring system according to a first embodiment of the present invention.

As shown in FIG. 1, a gas measuring system 0100 according to the first embodiment comprises, a gas sensor 0101, an electric power supply 0102 capable of generating an AC voltage of various frequencies, a measuring means 0103 for measuring an electric response from the gas sensor, and a gas desorbing means 0104 for desorbing gases which are adsorbed by the gas sensor.

In the following explanation, the gas sensor will first be described, followed by the principle of detecting gases and components other than the gas sensor.

(2) Structure of the Gas Sensor (A) Basic Structure

The gas sensor of the present invention comprises a gas detection device, a capacitive element, and a pair of electrodes. In the basic structure of the gas detection device, the pair of electrodes are electrically connected to electric terminals of an electric element comprising the gas detection device and the capacitive element.

Figure 2:
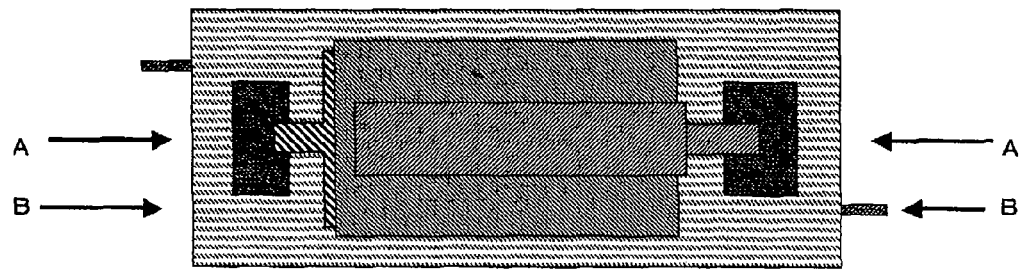
FIG. 2($a$) is a top view schematically showing the structure of a gas sensor according to the first embodiment of the present invention, FIG. 2($b$) is a cross-sectional view taken along line A-A in FIG. 2($a$), and FIG. 2($c$) is a cross-sectional view taken along line B-B in FIG. 2($a$).
Figure 2:
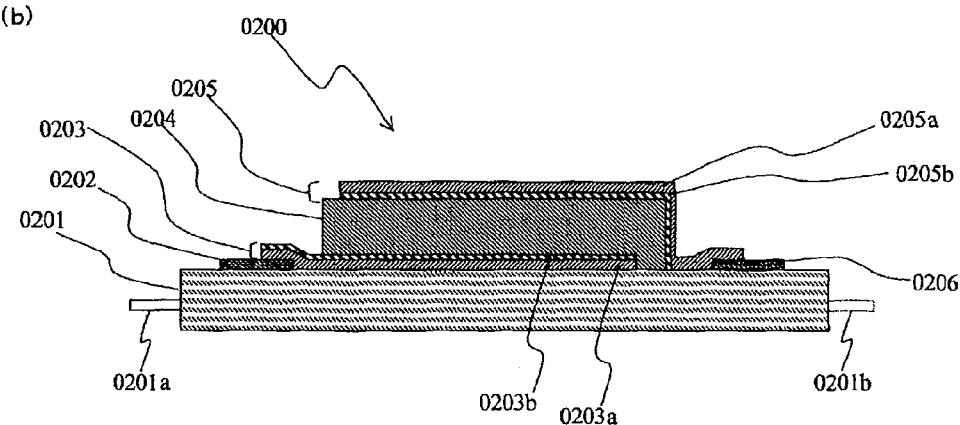
Figure 2:
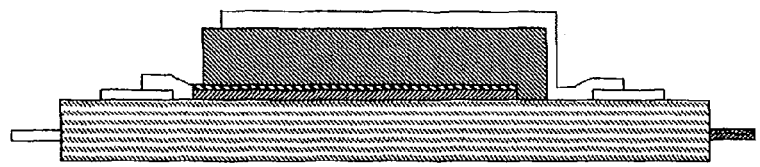

FIG. 2(*a*) is a top view schematically showing the structure of the gas sensor according to the first embodiment of the present invention. FIG. 2(*b*) is a cross-sectional view taken along line A-A in FIG. 2(*a*), and FIG. 2(*c*) is a cross-sectional view taken along line B-B in FIG. 2(*a*). A gas sensor 0200 according to the first embodiment comprises:

a ceramic heater 0201 which functions as a gas desorbing means;

a first gold layer 0202 and a second gold layer 0206 which are formed on the ceramic heater 0201 so that these gold layers have a prescribed distance from each other;

a first aluminum layer 0203 which covers a part of the surface of the first gold layer 0202, the covered part of the surface of the first gold layer being deviated to the side of the second gold layer 0206, and which covers a part of a region of the surface of the ceramic heater 0202 between the first and second gold layers 0202 and 0206, the covered part of the region being deviated to the side of the first gold layer 0202;

a gas detection device 0204 which covers a part of the surface of the first aluminum layer 0203, the covered part of the surface of the first aluminum layer being deviated to the side of the second gold layer 0206, and which covers a part of a region of the surface of the ceramic heater 0202 between the aluminum layer 0203 and the second gold layer 0206, the covered part of the region being deviated to the side of the first aluminum layer 0203; and a second aluminum layer 0205 which covers a part of the open top surface of the gas detection device 0204, the covered part of the open top surface being deviated to the side of the second gold layer 0206, and which covers a part of the surface of the second gold layer 0206, the covered part of the surface of the second gold layer being deviated to the side of the first gold layer 0202, and which has a connecting part which connects the above-described two parts.

The first and second aluminum layers 203 and 205 have metallic parts 0203*a* and 0205*a*, respectively, and oxide parts 0203*b* and 0205*b* which are formed at the interfaces facing the gas detection device 0204.

Dielectric layers including $C_{60}$ fullerene are formed near the interfaces between the oxide parts 203*b* and 205*b*, and the gas detection device 0204. Although the detailed structure of the dielectric layers is not clear, the structure is thought to consist of a dipole and/or an electric barrier. The capacitive element of the gas sensor according to the present invention consists of the oxide parts 0203*b* and 0205, and the dielectric layers. This capacitive element is connected in series with the gas detection device 0204.

A natural oxide film formed on the top surface of the second aluminum layer 0205 is not shown in FIG. 2. The gas sensor shown in FIG. 2 is illustrated in a manner such that the sensor is enlarged in the direction of lamination of layers. The enlargement ratio of the direction of lamination of layers to the direction normal to the above-described direction is almost 1000. Therefore, the member formed on the substrate 0201 is in the form of a film. Thus, the area of a part of the connecting part of the second aluminum layer 0205 where the connecting part contacts the gas detection device 0204 is much smaller than the area of a part of the second aluminum layer 0205 formed on the top surface of the gas detection device 0204. Accordingly, the region of the gas detection device 0204 facing the part of the second aluminum layer 0205 formed on the top surface of the gas detection device 0204 substantially forms the electric terminal of the gas detection device 0204 facing the second aluminum layer 0205.

The electric terminals of the electric element comprising the gas detection device 0204 and the capacitive element are composed of the interface of the oxide part 0203*b* facing the metal part 0203*a* of the part of the first aluminum layer 0203 where the first aluminum layer 0203 contacts the gas detection device 0204, and the interface of the oxide part 0205*b* facing the metal part 0205*a* of the second aluminum layer 0205, respectively. Therefore, the electrodes of the gas sensor according to the present embodiment are composed of the metallic part 0203*a* of the first aluminum layer 0203 and the metallic part 0205*a* of the second aluminum layer 0205, respectively. The first and second gold layers 0202 and 0206 are members provided for convenient connection to wires, and hence are not essential elements.

(B) Gas Detection Device

The gas detection device 204 of the present embodiment consists of a deposited film of $C_{60}$ fullerene, which is a dielectric semiconductor. As described above, it is possible for gases such as oxygen to penetrate into the deposited film of $C_{60}$ fullerene, and hence the region of adsorption of this gas detection device is not only the surface but also the entire body of the device.

Therefore, the electric conductivity of the gas detection device 204 of the present embodiment varies from $10^{-2}$ (ohm cm)$^{-1}$ to $10^{-10}$ (ohm cm)$^{-1}$, with the change in variation being at least eight Figures ($10^8$ times). Since the relative permittivity of $C_{60}$ fullerene is 4 to 5, the capacitance of the gas detection device 0204 is 40 pF when the area of the device is 1 mm$^2$ and the thickness of the device is 1 micrometer. The gas detection device in actual use is designed to have an area of 0.1 to 100 mm$^2$ and a thickness of 0.1 to 10 micrometers. Therefore, the capacitance of the gas detection device in actual use is 1 pF to 1 nF.

(C) Capacitive Element

The capacitive element of the present embodiment comprises the oxide parts 0203*b* and 0205*b*, which are formed at the interfaces of the first and second aluminum layers 203 and 205 facing the gas detection device 0204. The thickness of the oxide parts is generally 0.1 to 10 nm and typically 0.5 to 5 nm. Therefore, when the area of one of the electric terminals of the electric element is 1 mm$^2$, the capacitance of the capacitive element of the gas detection device is expected to be 1 to 100 nF.

As described below, the gas sensor increases in sensitivity as the capacitance of the capacitive element increases. From this viewpoint, it is preferable that the thickness of the oxide part be smaller. However, the oxide part functions as a barrier layer against charge injection from electrode contacting the oxide layer to the gas detection device. The charge injection makes the measurement of gases unstable, and this tendency becomes more marked as the frequency of the voltage applied to the gas sensor increases. Therefore, it is preferable that the oxide part have a certain thickness. Accordingly, the preferable thickness of the oxide part is 1 to 5 nm.

The above-described preferable range of the thickness of the oxide part is selected for the case in which the oxide part consists of aluminum. When another metal capable of forming a natural oxide such as titanium is employed, the preferable range of the thickness of the oxide part of the metal naturally differs from the range in the case of aluminum, because the permittivity and properties as an injection barrier layer of the oxide of the metal are different from those of aluminum.

As described above, dielectric layers which includes $C_{60}$ fullerene are formed near the interfaces between the oxide parts 203*b* and 205*b* and the gas detection device 0204. An experimental result regarding this dielectric layer is explained below.

The capacitance around the interfaces between the aluminum layers and the deposited film of $C_{60}$ fullerene was calculated by simulation of the equivalent circuit of the gas sensor of the present embodiment based on the results of evaluation of the gas sensor. Assuming that the calculated capacitance is originated only from the oxide part of aluminum, the thickness of the oxide part was calculated to be 6 nm. However, the thickness of the oxide part formed on the aluminum layer of the gas sensor was measured to be 1.0 nm by spectral ellipsometry. This result suggests that there is an additional dielectric layer which forms the capacitive element of the gas detection device in addition to the oxide part, that the additional dielectric layer other than the oxide part is positioned near the interface between the deposited film of $C_{60}$ fullerene and the oxide part, and that the capacitance of the additional dielectric layer corresponds to the capacitance of an oxide part having a thickness of 5 nm.

(D) Electrodes

The electrodes of the present invention are electric elements connected to the electrical terminals of the electric element comprising the gas detection device and the capacitive element. The electrodes in the present embodiment comprise metallic parts 0203*a* and 0205*a* of the first and second aluminum layers.

The electrodes may consist of metals such as gold, aluminum, and copper; electroconductive oxides such as ITO and ZnO; and electroconductive carbon materials such as a graphite and a metallic CNT.

However, it is preferable in the present embodiment that the electrodes consist of a metal capable of forming a dense natural oxide layer, because part of the capacitive element of the present embodiment consists of the natural oxide layer. Examples of such a metal include, in addition to aluminum, titanium, chromium, nickel, niobium, and tantalum.

(3) Method of Detecting Gases
(A) Principle of Detection

Figure 3:
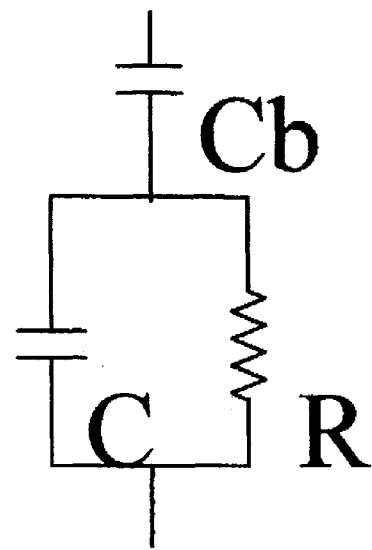
FIG. 3 is a partial circuit diagram showing an equivalent circuit of a gas sensor according to the first embodiment of the present invention.

The equivalent circuit of the gas sensor according to the present embodiment is shown in FIG. 3, where C and R represent the capacitance and resistance of the gas detection device, respectively, and $C_b$ represents the capacitance of the capacitive element.

In the gas measuring system according to this embodiment, an AC voltage is applied to the gas detection device having the equivalent circuit shown in FIG. 3, and the degree of adsorption of gases to the gas detection device is detected by measuring the change in an electrical response at the suitable applied voltage. "An electric response" includes all responses which are measured electrically as the response of gas adsorption on the gas sensor for the applied AC voltage. Therefore, a change in current may be measured. Impedance or admittance, which is the inverse of impedance, may be measured. The complex capacitance or the complex conductance of the gas sensor may be measured. Such an application of an AC voltage prevents the gas detection device having dielectric properties from charging on the device. Therefore, phenomena which reduce the accuracy of measurement such as drift are prevented. Accordingly, measurement with high accuracy is achieved.

(B) Measurement of Complex Capacitance

The case in which the complex capacitance is measured will be described below as a typical example. Measurement of the complex capacitance makes it possible to separate the combined effects appeared on the electric components of the gas sensor from each other. Specifically, the effects of the two capacitive components and the resistive component shown in FIG. 3 are independently isolated, whereby it is possible to effectively detect the variation of the resistive component, namely, the variation of the electric conductivity of the gas detection device.

First, the complex admittance $Y^*$ of the equivalent circuit shown in FIG. 3 is defined by Formula (1).

$$Y^* = \frac{\{\omega^2 C_b^2 R + j\omega C_b(1 + \omega^2 CR^2(C + C_b))\}}{1 + \omega^2 R^2 (C + C_b)^2} \tag{1}$$

As described above, C has a capacitance of 1 pF to several nF and $C_b$ has a capacitance of several tens of nF. Therefore, $C_b$ is much larger than C, so Formula (1) can be approximated as Formula (2).

$$Y^* \approx \frac{\omega^2 C_b^2 R + j\omega C_b(1 + \omega^2 CC_b R^2)}{1 + \omega^2 R^2 C_b^2} \tag{2}$$

The real part of the admittance $Y^*$, namely, the conductance G is defined by Formula (3).

$$G = \frac{\omega^2 C_b^2 R}{1 + \omega^2 R^2 C_b^2} \tag{3}$$

The dependence of the conductance G on the frequency of the AC voltage means that the conductance G increases as the frequency increases in a low-frequency zone, but that the conductance G directly indicates the conductance of the gas detection device in a high-frequency zone.

The relation between the admittance $Y^*$ of the gas sensor and the complex capacitance $C^*$ ($=C'-jC''$, where $C'$ represents the real part of $C^*$ and $C''$ represents the imaginary part of $C^*$), can be expressed by Formula (4).

$$Y^* = j\omega C^* = j\omega(C' - jC'') \tag{4}$$

Therefore, the real part of the complex capacitance $C^*$, which is referred to as a capacitance $C'$, can be expressed by Formula (5) under the assumption of $C_b$ much greater than C.

$$C' = \frac{1 + \omega^2 C_b C R^2}{1 + \omega^2 C_b^2 R^2} C_b \tag{5}$$

Thus, the dependence of the capacitance $C'$ on the frequency of the AC voltage shows that the capacitance $C'$ is almost equal to $C_b$ in a low-frequency zone, because both $\omega^2 C_b CR^2$ and $\omega^2 C_b^2 R^2$ are much smaller than 1. It also shows that the capacitance $C'$ is almost equal to C in a high-frequency zone, because both $\omega^2 C_b CR^2$ and $\omega^2 C_b^2 R^2$ are much larger than 1.

Figure 4:
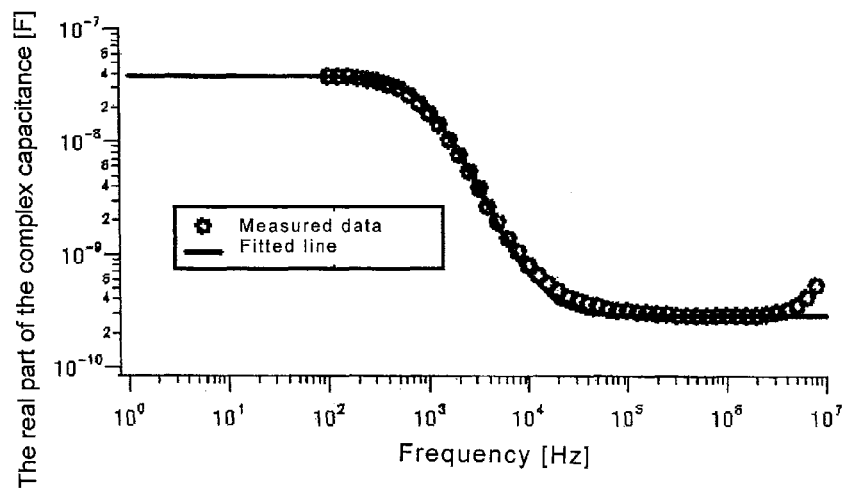
FIG. 4 is a graph showing one example of the capacitance profile obtained from a gas measuring system according to the first embodiment of the present invention and the fitted result for the obtained capacitance profile.

FIG. 4 is a graph showing the dependence of the capacitance $C'$ on the frequency of the applied AC voltage when the degree of the adsorption of gases to the gas detection device is stabilized by maintaining the temperature at 200 degrees C. and the ambient pressure at 10 Pa so as to maintain R at a constant value. The circles in FIG. 4 indicate measured values, and the solid line in FIG. 4 indicates a fitted curve calculated based on the equivalent circuit shown in FIG. 3.

As shown in FIG. 4, the capacitance $C'$ is almost equal to $C_b$ associated with the capacitive element, which is partly composed of the oxide parts of the aluminum layers, in a low-frequency zone of at most 200 Hz. However, the capacitance $C'$ decreases to C associated with the gas detection device, composed of $C_{60}$ fullerene, in a high-frequency zone of at least 100 kHz. An intermediate zone between the low-frequency zone and the high-frequency zone forms a transition zone. The absolute value in the variation of the capacitance $C'$ has local maximums near the edges of this transition zone.

When R is changed, the transition zone moves in response to the change of R, maintaining a basic profile such that the capacitance $C'$ has almost the same values in the low-frequency zone and the high-frequency zone, and such that the transition zone is disposed between these zones.

Figure 5:
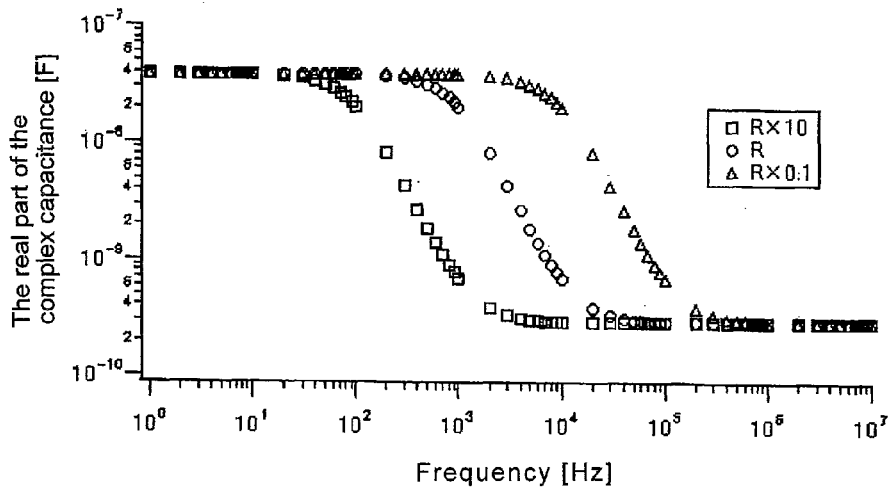
FIG. 5 is a graph showing the capacitance profiles calculated from a simulation of an equivalent circuit of a gas measuring system according to the first embodiment of the present invention.

FIG. 5 is a graph which illustrates the profile of the dependence of the capacitance $C'$ on the frequency obtained from a simulation of the equivalent circuit of the gas sensor according to the present embodiment. The graph shows that the transition zone shifts in the direction of the low-frequency zone as the value of R becomes larger although the shape of the transition zone is not modified, and that the transition zone shifts in the direction of the high-frequency zone as the value of R becomes smaller.

As described above, measuring the capacitance $C'$ of the gas sensor according to the present embodiment make it possible to detect a fall in the electric conductivity of the gas detection device caused by the adsorption of gases. The variation of the measured capacitance $C'$ ranges from almost $C_b$ as an upper limit to C as a lower limit. Therefore, $C_b$ should be larger than C, and it is preferable that the difference between them should be large as possible. From the viewpoint of stable measurement, the ratio $C_b$ to C is preferably at least 10, and it is especially preferable that the ratio be at least 100.

The capacitance $C'$ or an electric parameter based on the capacitance $C'$ such as relative permittivity may be used for measurement or displaying measured data. The above-described method of detecting gases can be also applied to a gas detection device having an electric conductivity which is increased by the adsorption of gases, in spite of the fact that this tendency is opposite on the tendency of the gas detection device according to this embodiment. The transition zone of the gas detection device having the opposite tendency shifts to the opposite direction when gases are adsorbed by the gas detection device of the gas sensor.

(C) Specific Method of Measurement

Several specific examples of the above-described method of detecting gases are as follows.

a) Fixed Frequency

First, an AC voltage is applied when gases are not adsorbed in the gas detection device. The frequency of the applied voltage is selected from a frequency in the transition zone, such as the frequency at the center of the transition zone. Then, the capacitance C' is continuously measured at the fixed frequency. When the electric conductivity of the gas detection device is decreased by the adsorption of gases, the transition zone shifts in the direction of the low-frequency zone and hence the capacitance C' at the fixed frequency decreases. Therefore, the change of the degree of adsorption of gases can be quantitatively evaluated by measuring the change of the capacitance C'.

When the frequency of the applied voltage is fixed in the transition zone, where the absolute value of the variation of the capacitance C' is a local maximum or a local minimum, namely, at a peak or a valley, the capacitance C' greatly changes due to a small amount of adsorption of gases. Therefore, this measuring method is suitable for the precise detection of gases.

When the frequency of the applied voltage is fixed at a frequency which is lower than the frequency where the capacitance C' is in a valley near the low-frequency zone, the change of the capacitance C' is small when the amount of adsorption of gases is small. However, the capacitance C' greatly changes when the amount of adsorption reaches a certain level. This measuring method can be applied together with the above-described precise measuring method to provide stepwise alarms warning of danger. Specifically, the gas sensor is measured at a plurality of frequencies, and an alarm is generated when gas leakage is detected by measurement at the frequency where the capacitance C' is near a valley and a signal which closes a system is issued when gas leakage is detected even by measurement at another frequency which is lower than the above-described frequency caused by an increase in the gas leakage.

b) Fixed Capacitance

Instead of the above-described measurement in which the frequency is fixed, the frequency may be modulated during measurement so that the measured value of the capacitance C' is maintained at a prescribed value. In this case, the resistance, namely the electric conductivity, is calculated from the modulated frequency, and the amount of adsorption of gases is estimated based on the calculated result.

c) Capacitance Profile

The profile of the frequency dependence of capacitance C', which may be referred to as the capacitance profile, may be obtained by continuously varying the frequency of the applied voltage during measurement. In this case, the resistance, namely the electric conductivity, of the resistive component of the gas detection device is calculated by analyzing the obtained capacitance profile, and the amount of adsorption of gases is estimated based on the calculated result. This method is expected to have a high precision, although the loads imposed on both the power supply and the measuring means become high enough.

(D) Effect of Temperature

In some gas detection devices, the resistance, namely the electric conductivity, of the resistive component of the gas detection device changes depending not only on the adsorption of gases but also on the temperature of the gas detection device. The gas detection device according to this embodiment also has characteristics such that the electric conductivity increases as the temperature increases. In this case, the effect of temperature on the measured data can be reduced based on reference data which have been previously measured and which contain the dependence of the electric conductivity on the temperature.

A reference sensor to which gases are not adsorbed can be installed near the gas sensor, and the difference between the data measured by the gas sensor and the data measured by the reference sensor can be regarded as the actual measured data. The reference sensor may have the same structure as the gas sensor except that the whole exposed region of the gas detection device in the reference sensor is sealed by a material which is not penetrated by gases, such as an organic material like a polyimide, or an inorganic material having a siloxane bond. The reference sensor can function as a temperature sensor having the same sensitivity to temperature as the gas detection device.

A ceramic heater is continuously operated during measurement and raises the temperature of the gas detection device so that a change of the ambient temperature does not affect the temperature of the gas detection device, although gases can be adsorbed to the gas detection device at the temperature of the detection device.

(E) Investigation of the Equivalent Circuit

Figure 6:
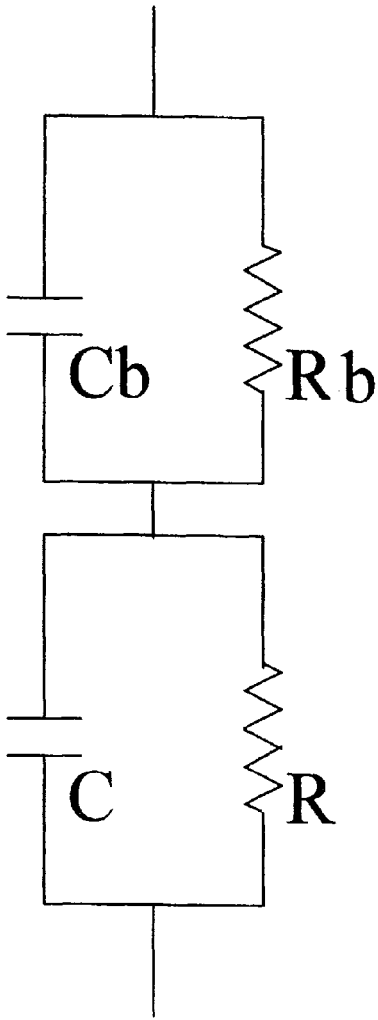
FIG. 6 is a partial circuit diagram showing an equivalent circuit of the gas sensor according to the first embodiment of the present invention, where the partial circuit diagram is necessary for strict interpretation of the gas sensor.

According to further investigations of the electric properties of the gas sensor according to the present embodiment, the capacitive element, which may comprise an oxide film, has not only a capacitive component $C_b$ but also a resistive component $R_b$. Therefore, the equivalent circuit of the gas sensor according to the present embodiment should be accurately expressed by the circuit shown in FIG. 6. The resistive component $R_b$ in the present embodiment is a resistive component at the interface between $C_{60}$ fullerene and aluminum, namely, an interfacial resistance. This interfacial resistance is thought to vary due to the adsorption of gases. Therefore, it may be possible to measure a much smaller amount of gases by properly analyzing this resistive component $R_b$.

Since the capacitance profile is largely affected by the capacitive component $C_b$ of the capacitive element in a high-frequency zone, the influence of the resistive component $R_b$ is small in a high-frequency zone of the capacitance profile. On the other hand, the capacitance C' increases in a low-frequency zone of the capacitance profile because of the influence of the resistive component $R_b$. However, the influence of the resistive component $R_b$ is not large in the transition zone of the capacitance profile. Therefore, as long as measurement of the degree of adsorption of gases to the gas detection device is performed by measuring the transition zone of the capacitance profile, the result of measurement is not awfully affected by the variation of the resistive component $R_b$.

(4) Components Other Than Gas Sensor

Components of the gas measuring system according to the present embodiment other than the gas sensor will be explained below.

(A) Power Source

There is no limitation on the power source as long as it can generate an AC voltage. The power source needs to be able to change the frequency of the output AC voltage when a profile of the dependence of the electric response on the frequency of the applied AC voltage, such as a capacitance profile, is measured. In this case, the frequency may be swept over a range such as from a higher frequency to a lower frequency and in the reverse direction. Alternatively, a voltage in which plural frequencies are superimposed may be applied, and then the profile data can be obtained by frequency analysis such as by Fourier analysis in the measuring means.

An AC voltage having a sine wave profile is applied in the present embodiment, but there are no limitations on the wave profile. The wave profile may be a rectangular wave or a triangle wave as long as the applied voltage periodically varies and reverses in polarity, namely, as long as the wave profile of the voltage is repeatedly applied in a prescribed period, and the wave profile causes the electric potential at one electrode relative to another electrode to alternate between positive and negative. The center value of the applied voltage may be zero, or it may be shifted in the positive direction or the negative direction.

The maximum of the absolute value of the voltage applied by the power source is not limited as long as the maximum value is less than the dielectric breakdown voltage of the gas detection device. The dielectric breakdown voltage depends on the material and the structure of the gas detection device. For example, the voltage is about 10V when the detection device is made of $C_{60}$ fullerene and has a thickness of 1 micrometer. When the maximum value is excessively low, the effect of noise in the electric response increases. Therefore, the value should be properly defined in consideration of the effect. A gas detection device consisting of $C_{60}$ fullerene is preferably measured at 20 to 100 mV.

(B) Measuring Means

The measuring means may consist of a general purpose LCR meter capable of measuring the impedance or admittance. In this case, the capacitance C' can be calculated from the output data. The measuring means can preferably measure output parameters such as the resistance, the reactance, the conductance, and the susceptance. It is more preferable that the measuring means can directly output the capacitance C'. It is especially preferable that the means be integrated with the power source and be capable of measuring the desired profile.

(C) Gas Desorbing Means

The gas desorbing means is provided for desorbing gases which have been absorbed in the gas detection device and have changed the electric conductivity of the gas detection device. The ceramic heater which also functions as the substrate of the gas sensor functions as the gas desorbing means. Heater wires 0201a and 0201b of the ceramic heater 0201 shown in FIG. 2 are connected to an unillustrated power source for heating. When the power source for heating is operated so as to heat the ceramic heater 0201, the gas detection device 0204 is heated. Gases adsorbed in the gas detection device 0204 are then desorbed.

As described above, the simplest means for desorbing gases is a heating means, and a ceramic heater is employed as one example of this means. Therefore, a carbon heater or a resistive heater may be used instead of a ceramic heater as long as it can function as a gas desorbing means. The gas desorbing means may be an infrared lamp, a laser, or a means for bombarding the gas detection device 0204 by high-energy particles such as electrons.

Gases may be desorbed by reducing the partial pressure of the gases to be desorbed in the ambient environment of the gas sensor. In this case, the gas desorbing means consists of an exhaust means such as a rotary pump, a cryopump, a turbo-molecular pump, a diffusion pump, and a sublimation pump; and a gas supply means comprising a regulator, and a gas cylinder containing an inert gas such as high-purity nitrogen and argon.

A start-up process and a regenerating process using the gas desorbing means will be explained below.

a) Start-up Process

The object of the gas measuring system according to the present embodiment is to start the measurement of gases from a condition in which almost no gases to be measured, which may be referred to active gases so-called active materials, are adsorbed, and to detect an extremely small amount of the active materials, the content of which may be sub-ppm to ppb, and in some cases ppt in the ambient environment. Therefore, the start-up process is preferably performed before starting the measurement so that active materials are desorbed from the gas detection device. Specifically, in the process, the gas desorbing means is activated to heat the gas detection device, and/or the gas detection device is exposed to a vacuum environment or an inert gas atmosphere such as high-purity nitrogen.

The gas detection device may be covered with a covering layer or an electrode so as to block the gas detection device from being exposed to the ambient environment before use, and the gas detection device can be exposed to the measurement environment by breaking or removing the covering layer or the like. In this case, the start-up process is to expose the gas detection device to the measurement environment, and the gas desorbing means is not used.

b) Regenerating Process

In the gas detection device according to the present embodiment, active materials change the electric conductivity of the gas detection device by directly or indirectly transferring electrons to the active materials from $C_{60}$ fullerene. However, the change in electric conductivity occurs even when the active materials do not interact with the fullerene materials to generate a strong chemical bond. Therefore, most interactions between materials which affect the variation of the electric conductivity of the gas detection device are reversible.

Thus, the electric conductivity which has decreased due to the adsorption of active materials can be restored to the original level by activating the gas desorbing means to heat the gas detection device or exposing the gas detection device to a vacuum or an inert gas atmosphere such as high-purity nitrogen. By means of this regenerating process, the gas sensor can be repeatedly used.

(D) Temperature Measuring Means

The gas measuring system preferably comprises a temperature measuring means for measuring the temperature of the gas detection device, because the electric conductivity of the gas detection device according to the present embodiment also changes as the temperature changes. Any known means such as a thermocouple can be employed for the temperature measuring means. It is preferable to employ a device as a temperature measuring means having the same structure for both the gas detection device and the reference sensor which is sealed so that no gas is adsorbed in the sensor of the temperature measuring means. In this case, the effect of temperature on the gas sensor can be accurately reduced by using the data of the temperature measured in the reference sensor as reference data.

(5) Process of Manufacturing Gas Sensor

The process of manufacturing the gas sensor according to the present embodiment is explained below.

Basically, gold, aluminum, $C_{60}$ fullerene and aluminum are sequentially deposited through proper masks on a ceramic heater which also functions as a substrate. After forming layers by deposition, the deposited layers are exposed to an atmosphere containing oxygen such as the ambient air for one hour. Oxygen diffuses in the layer of $C_{60}$ fullerene, and an oxide film is formed at the interfaces of the layers of aluminum facing the $C_{60}$ fullerene deposited layer.

When the process includes a step in which the aluminum layer (reference 0203 in FIG. 2) formed between the substrate and the $C_{60}$ fullerene deposited layer is exposed to the ambient air before the $C_{60}$ fullerene is deposited on the layer, a natural oxide film is easily formed at the interface of the aluminum layer facing the $C_{60}$ fullerene deposited layer without the above-described exposure to the ambient air. The surface of the aluminum layer may be forcibly oxidized before depositing $C_{60}$ fullerene in order to ensure the formation of an oxide layer on the aluminum layer.

(6) Gas for Measurement

A substance can be an object for measurement when the substance can directly or indirectly exchanges an electron with $C_{60}$ fullerene forming the gas detection device and change the electric conductivity of the gas detection device by the adsorption of the substance. Specifically, since $C_{60}$ fullerene is an electric conductive semiconductor, oxygen and water are typical examples of a gas for measurement.

Examples of the gas for measurement also include hydrogen, alcohols such as ethanol, aldehydes such as formaldehyde, ketones such as acetone, nitrogen-containing compounds such as ammonia and methylamine, aromatic compounds such as benzene, acid compounds such as $NO_X$ and $SO_X$, and halogen-containing compounds such as hydrogen chloride and gaseous chlorine.

The gas for measurement can be selected by changing the material composing the gas detection device and the sensitivity of the gas for measurement is also controllable. For example, when a gas detection device consisting of $C_{60}$ fullerene is found to be relatively less sensitive, a gas detection device having higher sensitivity can be obtained by selecting a substance which can easily interact with the gas for detection, such as a chemically-modified fullerene, an endohedral fullerene, and a heterofullerene, as a whole or partial component of the gas detection device.

(7) Application

The gas sensor according to the present embodiment has a high sensitivity, and its size can be reduced compared to a conventional gas sensor such as a sensor using a mass analyzer. Therefore, a gas measuring system comprising this gas sensor can be used in various ways such as in a manufacturing process for semiconductor devices and as a fuel cell. Application to a manufacturing process for semiconductor devices will be explained below as one example.

There is an extremely strong demand for minimizing the contamination concentration in manufacturing processes for semiconductor devices. The permissible concentration of oxygen or water contaminant in gaseous nitrogen is now less than 5 ppb, and it will be necessary to reduce the content to less than 1 ppb in 2010. Currently, a mass analyzer is generally employed as a means for measuring such an extremely small amount of gases. However, it is impossible to apply this means to each gas pipe of equipment, because the size of the mass analyzer is so large that it can be installed only at a process chamber.

However, when the contaminant content is measured only in the process chamber in spite of a severe demand for the contaminant content to be controlled at the ppt level, once contamination occurs in the gas supplying system for processing, it takes a long time to restore the quality of products. Therefore, it is difficult to control the lead time of products in this case.

Thus, it becomes necessary to install a high gas sensor at each pipe of equipment and prevent contamination of the process chamber. Accordingly, there is a strong desire for development of a high-sensitivity gas sensor having an extremely compact size.

The gas sensor according to the present embodiment is sufficiently small and so highly sensitive that the sensor is capable of measuring contaminant gases not only at a ppb level but also at a ppt level. Therefore, it is possible to meet the above-described severe demand by installing the gas sensor according to the present invention on the piping for each piece of equipment.

(8) Variation of the Gas Sensor According to the First Embodiment (A) Capacitive Element Consisting of Materials Other Than an Oxide Film A natural oxide film spontaneously formed at the interface of the metallic layer facing the gas detection device is used as a part of a capacitive element in the present embodiment. However, as described above, an oxide film which has been actively oxidized can be used instead of a natural oxide film. Alternatively, a modified layer with dielectric properties on the metallic layer prepared by modifying the surface of the metallic layer such as by carbonizing or nitriding may be used instead of an oxide film. A modified layer and an oxide layer are generically referred to as a modified dielectric layer.

Alternatively, the metallic layer may consist of a material which substantially does not form an oxide layer such as gold, which is referred to as an inert metal layer, and a member constituting the capacitive element may be installed without forming the modified dielectric layer. There are two possible methods of installation. One method is to form the member so as to be integrated with the gas detection device, and the other is to form the member so as to be discrete from the gas detection device.

a) Integrated Formation of the Added Dielectric Layer

Figure 7:
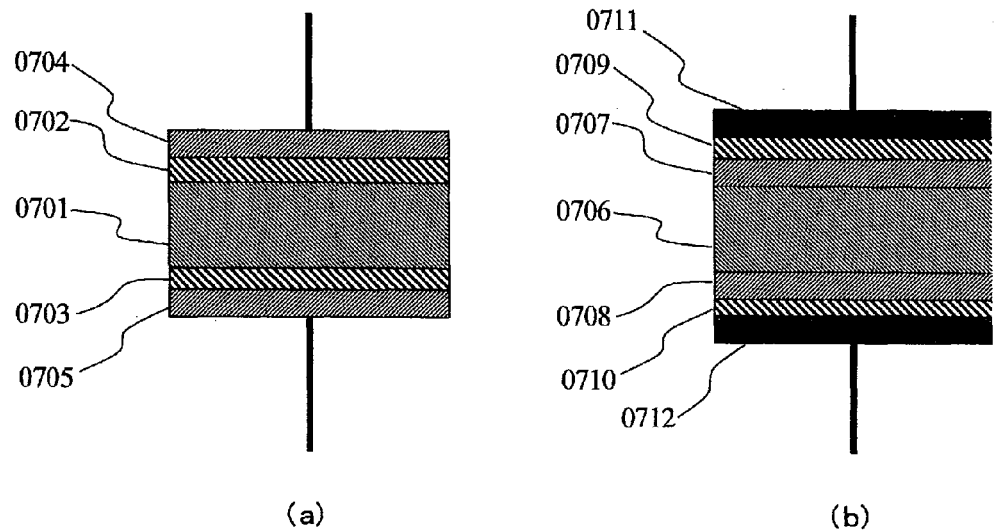
FIG. 7 are schematic views showing the structures of variations of a gas sensor according to the first embodiment of the present invention. In the variations, a capacitive element of an added dielectric layer, an explanation of which will be given below, is integrated with the gas detection device. In particular, the added dielectric layer is formed between the gas detection device and the inert metal layer as shown in (a), and an inert metal layer, an explanation of which will be given below, is formed directly on the surface of the gas detection device with the added dielectric layer, and otherwise the added dielectric layer is formed on the outer side of the inert metal layer which is shown in (b).

When the capacitive element is integrated with the gas detection device, the advantage is obtained that the size of the gas sensor is small. In this case, there are two configurations. In a first configuration, as shown in FIG. 7(*a*), in a manner similar to the oxide film, dielectric layers 0702 and 0703, which may be referred to as added dielectric layers, are disposed between the gas detection device 0701 and metallic layers, namely, inert metal layers 0704 and 0705. In a second configuration, as shown in FIG. 7(*b*), inert metal layers 0707 and 0708 are directly formed on electric terminals of a gas detection device 0706, and added dielectric layers 0709 and 0710 are disposed on the inert metal layers 0707 and 0708, respectively.

In the first configuration, the inert metal layers 0704 and 0705 form "electrodes" of the gas sensor. However, in the second configuration, the inert metal layers form members electrically connecting "the gas detection device" and "the capacitive element", and electrodes 0711 and 0712 have to be disposed on electric terminals of the added dielectric layers 0709 and 0710.

A material composing the added dielectric layers is typically an insulator such as $SiO_2$, and preferably a material having a high permittivity such as $HfO_2$-type materials and $BaO—R_2O_2—TiO_2$-type materials, because the sensitivity of the gas sensor increases as the capacitance of the capacitive element becomes higher. Since the added dielectric layer preferably functions as an anti-charge injection layer to the gas detection device, the thickness of the added dielectric layer is preferably at least 1 nm so that a tunneling phenomenon is prevented.

An electric element consisting of the inert metal layers and the gas detection device sandwiched between the inert metal layers is referred to as a gas detection module. This module does not substantially contain an electric element which has dielectric characteristics other than the gas detection device.

b) Connection of an External Capacitor

Figure 8:
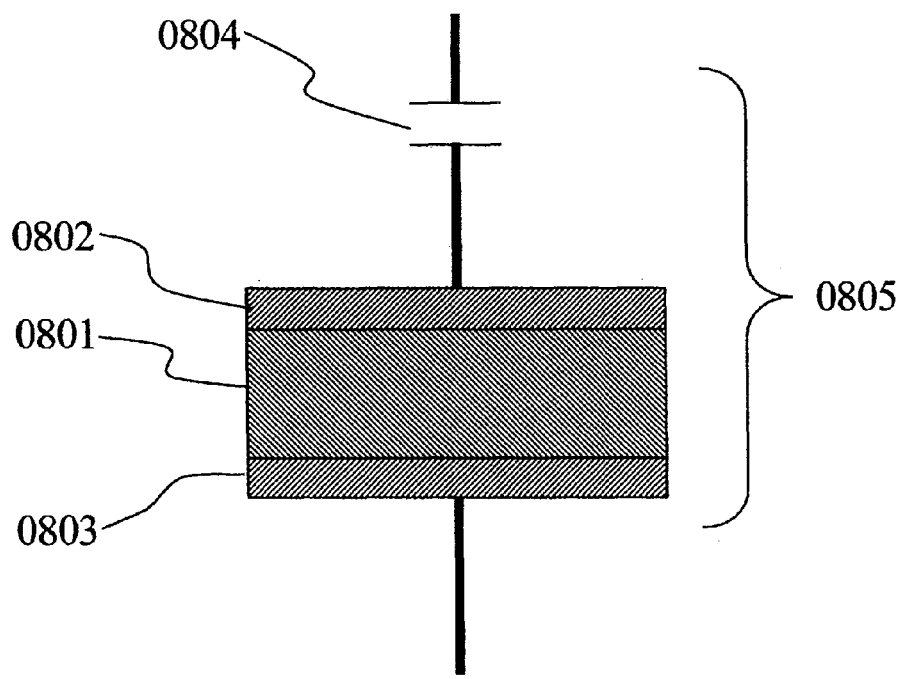
FIG. 8 is schematic view showing the structure of a variation of the gas sensor according to the first embodiment of the present invention. In the variation, a capacitive element is discretely formed from the gas detection device.

When the capacitive element is discretely formed with respect to the gas detection device, as shown in FIG. 8, as a basic configuration, inert metal layers 0802 and 0803 are disposed on electric terminals of a gas detection device 0801, and a capacitor 0804 is connected in series to the gas detection module. In this configuration, the gas sensor 0805 is defined by all of the above components, and the inert metal layer 0803 to which the capacitor is not connected and an electrode of the capacitor 0804 which does not face the gas detection device compose the "electrodes" of the gas sensor. This configuration has the advantage that the discrete capacitor 0804 can design freely as the capacitive element because the size of the capacitor 0804 is independent of the size of the gas detection device 0801. For example, when the gas sensor is used to detect the existence of gases, a capacitor having a low capacitance can be employed so as to minimize the size or reduce the cost of the gas sensor. When a large range of quantitative measurement is required, a capacitor having a high capacitance is connected so as to enlarge the dynamic range.

When an oxide film is used as the capacitive element, it is necessary to control the thickness of the oxide film in the manufacturing process. However, when a configuration consisting of a gas detection module and an external capacitor is employed, the strictness of thickness control can be reduced because a commercially available capacitor can be used as the capacitive element.

(B) Combination of Integrated Configuration and Discrete Configuration

Figure 9:
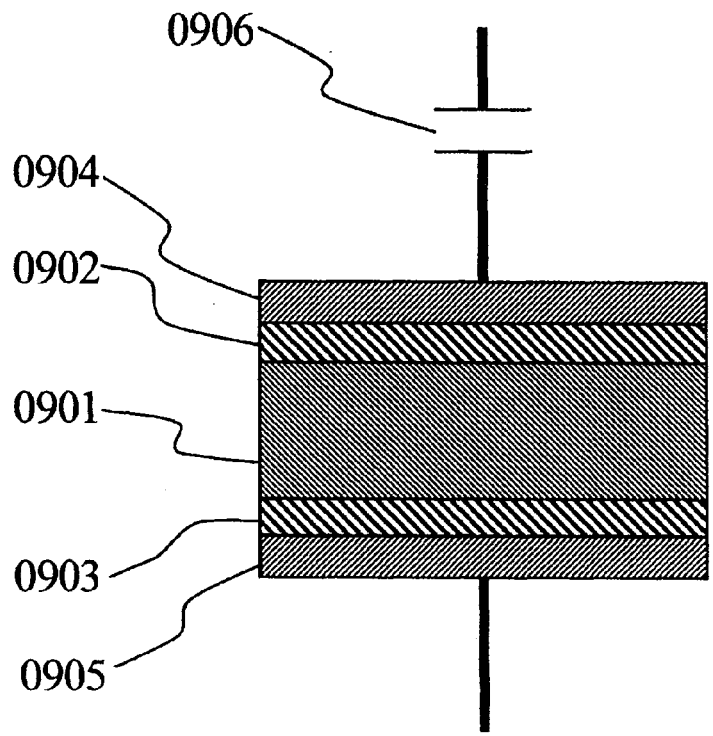
FIG. 9 is schematic view showing the structure of a variation of the gas sensor according to the first embodiment of the present invention. In the variation, the capacitive element consists of two parts. One part of the capacitive element is integrated with the gas detection device, and the other part of the capacitive element is formed separately from the gas detection device.

The above-described two configurations can be employed to obtain a configuration in which a discrete capacitor is connected to a gas detection device having a dielectric layer integrated with the gas detection device. In FIG. 9, as an example, a gas sensor is shown which has a configuration in which a capacitor 0906 is connected in series to an electric element in which added dielectric layers 0902 and 0903 are formed on electric terminals of a gas detection device 0901, and inert metal layers 0904 and 0905 are formed at both end surfaces of the dielectric layers.

This configuration is expected to enable more stable measurement than the configuration shown in FIG. 8, because the possibility of charge injection is smaller. In this configuration, the capacitance of the whole capacitive element is affected more by the element having a lower capacitance between the added dielectric layer and the discrete capacitor. Therefore, when the difference in capacitance between them is excessive, the effect of the element having a higher capacitance becomes negligible. Thus, it is preferable that the ratio of capacitance of these elements be 0.1 to 10 and that a discrete capacitor be used for adjustment. For example, a laminated structure consisting of a metal film, an insulator film, and a metal film is formed as an external capacitor on the substrate on which the gas sensor is also formed adjacent to the external capacitor. The capacitance of the laminated structure can be adjusted by trimming its shape, and particularly the area of films, by means such as a laser. When the capacitance of the whole capacitive element of the resulting gas sensor is higher than the designed capacitance, the external capacitor is partially trimmed so that the capacitance of the whole capacitive element falls within the design range.

When the discrete capacitor has a tunable capacitance, it becomes possible to reduce the step of adjusting the capacitance of the whole capacitive element in the manufacturing process. In this case, the capacitance of the whole capacitive element can be adjusted when measurement is performed. Therefore, this configuration is suitable for applications in which the degree of adsorption of gases needs to be quantitatively measured.

(C) Other Structures of the Gas Sensor

The gas sensor according to the present embodiment has a structure such that the direction normal to the surfaces of electric terminals of the gas detection device, namely the direction of the electric field of the gas detection device, substantially corresponds to the direction of lamination of the gas detection device on the substrate. This structure can be defined as a laminated structure or a sandwiched structure. However, the gas sensor may have a structure other than this structure.

For example, the above-mentioned direction of the electric field can be perpendicular to the direction of lamination. In one specific structure of this type, two electrodes having the shape of a comb are formed on the substrate so that comblike parts of electrodes engage with each other with a prescribed gap and the modified dielectric layers or the added dielectric layers are formed on the surface of the electrodes. A constituent material of the gas detection device is deposited so that the surface of the substrate exposed at the gap between the comblike parts of electrodes and the sidewalls of the comblike parts facing the gap are covered with the constituent material of the gas detection device. A gas sensor is then formed in which the modified dielectric layers or the added dielectric layers formed on the sidewalls of comblike parts facing the gap compose the capacitive element and the direction of the electric field is perpendicular to the direction of lamination.

In this structure, the region of the gas detection device where gases are to be adsorbed, namely, the part of the gas detection device sandwiched between the capacitive elements is exposed. Therefore, this structure has the advantage that gases are rapidly adsorbed, and hence gases are measured in a high-responsive manner.

(D) Other Methods of Measurement

Figure 10:
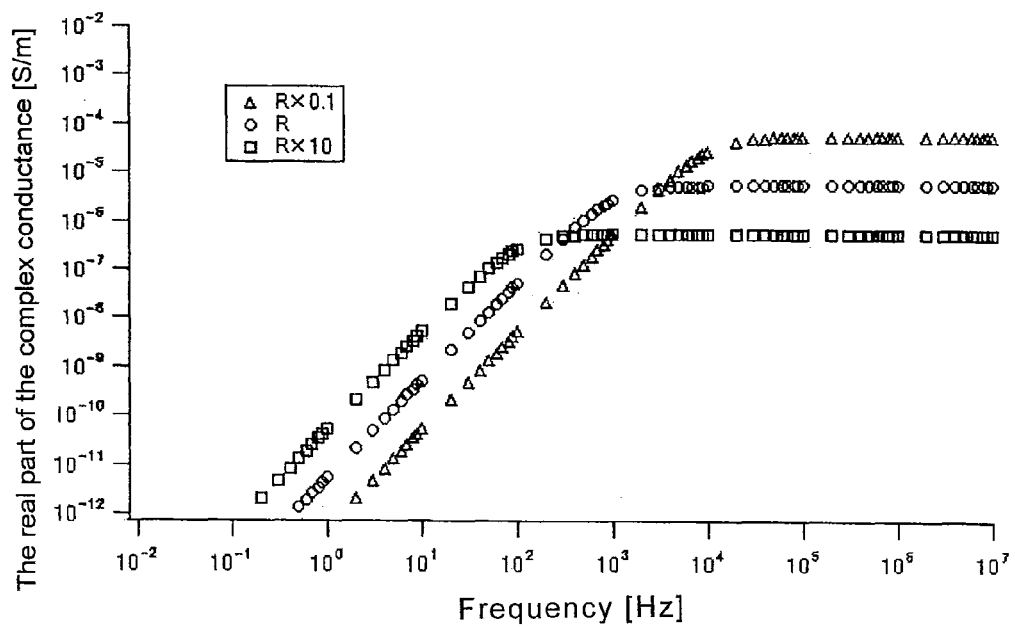
FIG. 10 is a graph showing conductance profiles calculated from a simulation of an equivalent circuit of the gas measuring system according to the first embodiment of the present invention.

Although the complex capacitance is measured in the present embodiment, other electric responses such as the conductance shown by Formula 3 may be measured. A profile of the dependence of the conductance on the frequency of the applied AC voltage is shown in FIG. 10. The conductance is obtained by simulating the equivalent circuit shown in FIG. 3. The profile may be referred to as a conductance profile. FIG. 10 shows that the conductance profile varies due to variation of the resistive component R of the gas detection device. This figure also shows that the variation of R can be measured as the change of the conductance when the frequency is about 1 MHz and that the variation of R can be measured by tuning a frequency of the AC voltage such that a prescribed conductance is always obtained in a lower-frequency range of less than 1 MHz. The variation of R can also be measured by continuously adjusting the frequency where the local minimal value of the differential data of the conductance profile is obtained.

4. Second Embodiment

A gas measuring system according to a second embodiment of the present invention is explained below.

(1) Composition

The basic composition of the gas measuring system according to the second embodiment of the present invention is identical to the basic composition of the gas measuring system according to the first embodiment shown in FIG. 1. Namely, the gas measuring system according to the second embodiment also comprises components that respectively function as the gas sensor, an electric power supply capable of generating an AC voltage having different types of frequency, a measuring means for measuring the electric response from the gas sensor, and a gas desorbing means for desorbing gases which is adsorbed to the gas sensor. The components except for the gas sensor are the same as the constituents of the first embodiment.

(2) Gas Sensor

The gas sensor according to the present embodiment comprises a gas detection device containing a dielectric semiconductor, the electric conductivity of the gas detection device varying in response to the degree of adsorption of gases to the gas detection device, and a pair of electrodes which are connected to the gas detection device. Desired characteristics of the dielectric semiconductor are identical to those in the case of the gas sensor according to the first embodiment. The gas detection device is also composed of a deposited film of $C_{60}$ fullerene in the present embodiment, but other gas detection devices composed of other materials may be used.

Specifically, the structure of the gas sensor according to the present embodiment is the same as the structure shown in FIG. 2 except that the aluminum layers of the gas sensor shown in FIG. 2 are replaced by gold layers which form inert metal layers. Therefore, the gas sensor according to the present embodiment does not contain an element forming a capacitive element. Namely, the gas sensor according to the present embodiment consists of a pair of inert metal layers forming the electrodes and a gas detection device sandwiched between the electrodes.

(3) Method of Detecting Gases

Figure 11:
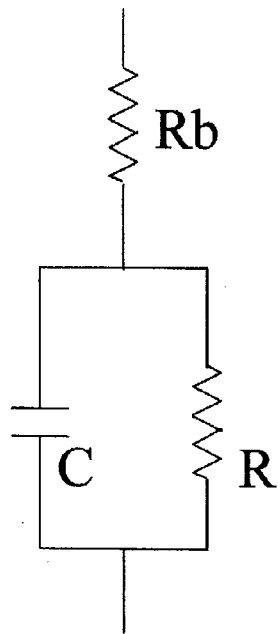
FIG. 11 is a partial circuit diagram showing an equivalent circuit of a gas sensor according to a second embodiment of the present invention.

The equivalent circuit of the gas sensor according to the present embodiment is shown in FIG. 11, where C and R represent the capacitive component and resistive component of the gas detection device, respectively, and $R_b$ represents the resistance of the inert metal layers forming the electrodes.

In the gas measuring system according to the present embodiment, an AC voltage is applied to the gas detection device having the equivalent circuit shown in FIG. 11, and the degree of adsorption of gases in the gas detection device is detected by measuring the electrical response which changes in response to the applied voltage. The application of the AC voltage prevents the gas detection device having dielectric properties from charging. Therefore, phenomena which cause a reduction in the accuracy of the measurement such as a drift are prevented. Accordingly, measurement with high accuracy is achieved.

A case in which the conductance is measured will be explained below as a typical example. Firstly, the admittance Y* of the partial circuit is defined by Formula (6).

$$Y^* = \frac{R + R_b + \omega^2 C^2 R^2 R_b + j\omega CR^2}{(R + R_b)^2 + \omega^2 C^2 R^2 R_b^2} \quad (6)$$

$R_b$ is much less than R because the thickness of the inert metal layers is normally at most 0.1 micrometers, although the thickness slightly varies depending on the material of the inert metal layer or the process of depositing the material. Therefore, Formula (6) can be approximated by Formula (7).

$$Y^* \cong \frac{(1/R) + \omega^2 C^2 R_b + j\omega C}{1 + \omega^2 C^2 R_b^2} \quad (7)$$

The real part of the admittance Y*, namely, the conductance G is written as Formula (8).

$$G = \frac{(1/R) + \omega^2 C^2 R_b}{1 + \omega^2 C^2 R_b^2} \quad (8)$$

Figure 12:
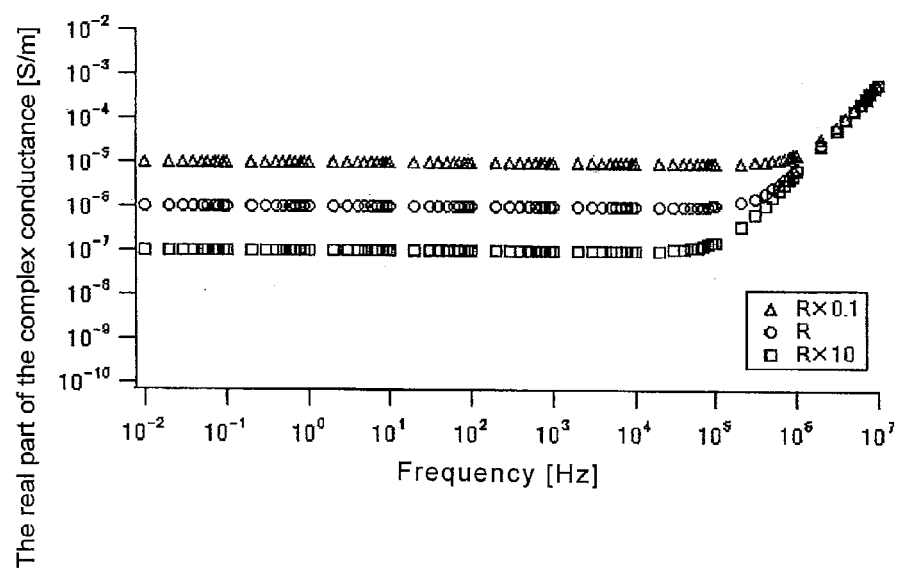
FIG. 12 is a graph showing conductance profiles calculated from a simulation of an equivalent circuit of the gas measuring system according to the second embodiment of the present invention.

Therefore, the dependence of the conductance G on the frequency of the AC voltage shows that the conductance G directly indicates the electric conductivity of the gas detection device in the low-frequency zone because the conductance G closes to (1/R), and it shows that the conductance G increases in the high-frequency zone as shown in FIG. 12.

Accordingly, the electric conductivity can be directly measured by measuring the conductance of the gas sensor of the present embodiment when the measured frequency is less than a prescribed frequency. In addition, a more stable measurement is achieved in comparison with the application of a DC voltage because the application of an AC voltage prevents the effect of a charging phenomenon.

The conductance profile has a shape in which the conductance is almost constant in a lower-frequency range and in which the conductance increases as the frequency becomes higher when the frequency is in a higher-frequency range. Therefore, there is a frequency where the frequency dependence of the conductance of the profile changes from constant to increasing. Since the frequency at which there is a change in the frequency dependence of the conductance profile varies in accordance with the electric conductivity of the gas detection device, the variation of the electric conductivity of the gas detection device can be measured by continuously measuring the conductance profile, differentiating each measured conductance profile, and obtaining a frequency where the conductance is at a peak in the differentiated profile. The variation of the obtained frequency then corresponds to the variation of the electric conductivity of the gas detection device.

EXAMPLE 1

Although the present invention will be explained in detail below by examples, it should be understood that the scope of the present invention is not limited to the examples.

First, the basic operation of the gas sensor according to the present invention will be explained by Examples 1-1 to 1-4, and Comparative Example 1-1.

(1) Example 1-1

A glass substrate with 30 mm×30 mm in area and a thickness of 0.12 to 0.17 mm was prepared. The substrate was placed in a vacuum chamber in which the pressure was $1\times10^{-5}$ Pa and the content of residual oxygen was at most 10 ppb, namely, at most $10^{11}$ molecules/cm$^3$. A pattern having the shape of a rectangle (20 mm×4 mm) as a lower electrode and a pattern contacting the rectangular pattern and having the shape of a line as a drain electrode were then formed by depositing aluminum. The thickness of these patterns was almost 100 nm.

A boat made of molybdenum and filled with $C_{60}$ fullerene, (Nanom Purple, which is a product of Frontier Carbon Co. Ltd,) was heated in the chamber. The temperature of the molybdenum boat was measured during the heating and was controlled to be in the range of 500 to 550 degrees C. so as to sublimate $C_{60}$ fullerene. A film of $C_{60}$ fullerene having a thickness of 2 micrometers was formed by the sublimation on the above-described aluminum pattern forming the lower electrode. The $C_{60}$ fullerene film had a rectangular shape so as to completely cover the underlying aluminum pattern.

A pattern of aluminum having the identical shape as the aluminum pattern forming the lower electrode was deposited on the $C_{60}$ fullerene film. The aluminum pattern had a thickness of 200 nm. A drain electrode for this pattern was also formed by depositing aluminum so as not to overlap the drain electrode for the lower electrode.

This layered structure formed by the above-described process was then taken out from the chamber and subjected to an air-exposure process comprising exposure to the ambient air for two hours. The structure after the process was performed, namely, a gas sensor, was placed in a measurement chamber. The pressure in the chamber was maintained at $1\times10^{-5}$ Pa and the content of residual oxygen was at most 0.1 ppb. High-purity nitrogen in which the content of oxygen was reduced to at most 0.1 ppb by a titanium sublimation pump, this nitrogen being referred to as pure nitrogen gas, was introduced into the chamber until the total pressure in the chamber reached 1 atm. A carbon heater was attached to the surface of the glass substrate of the gas sensor opposite to the surface on which deposited layers were formed. The carbon heater was heated for 6 hours so that the temperature of the surface of the gas sensor was maintained at 280±10 degrees C. to perform a start-up process.

After the start-up process, the carbon heater was adjusted so that the temperature at the surface of the gas sensor was maintained at 250 degrees C. Connectors from an impedance analyzer, which was a model LF4192A of Agilent Technologies, Inc., were then connected to one of the two drain electrodes.

An instrument for introducing gases which is capable of blending a plurality of gases in an arbitrary ratio by controlling a plurality of gas lines was previously attached to the chamber. This instrument can alternatively introduce the pure nitrogen gas at 1 L/minute and a blended gas having a total pressure of 1 atm at 1 L/minute. The blended gas consisted of the pure nitrogen gas and oxygen which was blended so that the oxygen content of the blended gas was 1 ppm. The blended gas will be referred to as nitrogen gas containing 1 ppm of oxygen. A mass spectrometer, which was a model API-500 of Nippon API Co., was also previously attached to the chamber. This spectrometer can measure an arbitrary gas even when the content of the gas is at a ppm level at atmospheric pressure.

After contacting the connectors with the drain electrodes, the instrument was activated, and the pure nitrogen gas was introduced into the chamber. After confirming that the pressure in the chamber had stably reached 1 atm, an AC voltage of 20 mV at 1 MHz was applied to the electrodes and the impedance of the gas sensor was measured once every minute. The relative permittivity was calculated based on the measured impedance, and the variation in the relative permittivity was recorded.

After starting the measurement, the gas line of the instrument for introducing gases was switched so that the gas sensor located in the chamber was exposed to the nitrogen gas containing 1 ppm of oxygen.

Figure 13:
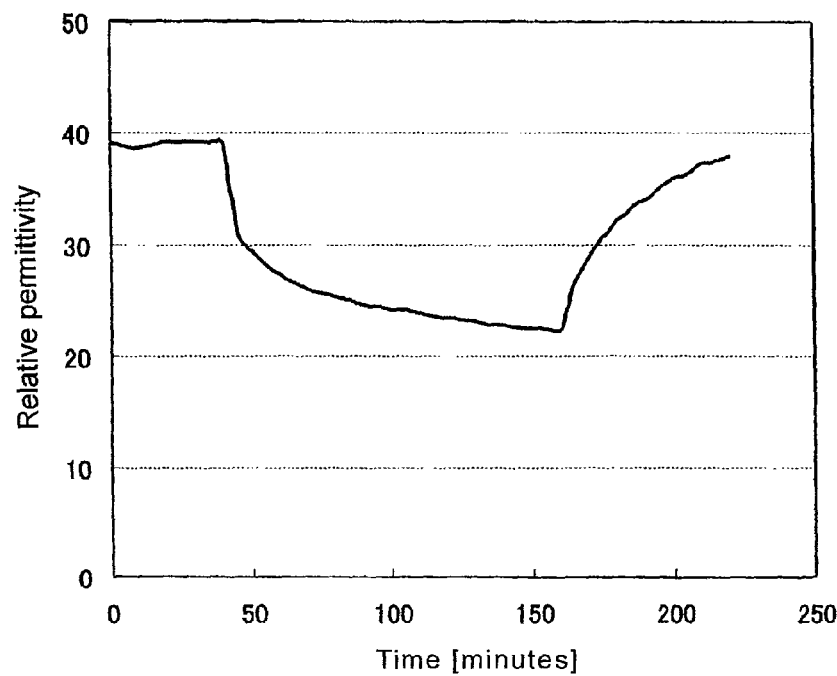
FIG. 13 is a graph showing the result of measuring oxygen at 250 degrees C. by the gas sensor according to Example 1-1.

Just after introducing the nitrogen gas containing 1 ppm of oxygen, a sharp decline of the relative permittivity (from 40 to 30) was measured as shown in FIG. 13. This means that the relative permittivity continuously decreased while the rate of decrease fell over time.

120 minutes after introducing the nitrogen gas containing 1 ppm of oxygen, the gas line was again switched so that the pure nitrogen gas was introduced into the chamber. It was found that the relative permittivity increased from 22 to about 38 in one hour when the temperature was maintained at 250 degrees C. When the temperature was increased to 280 degrees C., the relative permittivity recovered to 40, which was the initial value of the relative permittivity before introducing the nitrogen gas containing 1 ppm of oxygen.

(2) Example 1-2

Figure 14:
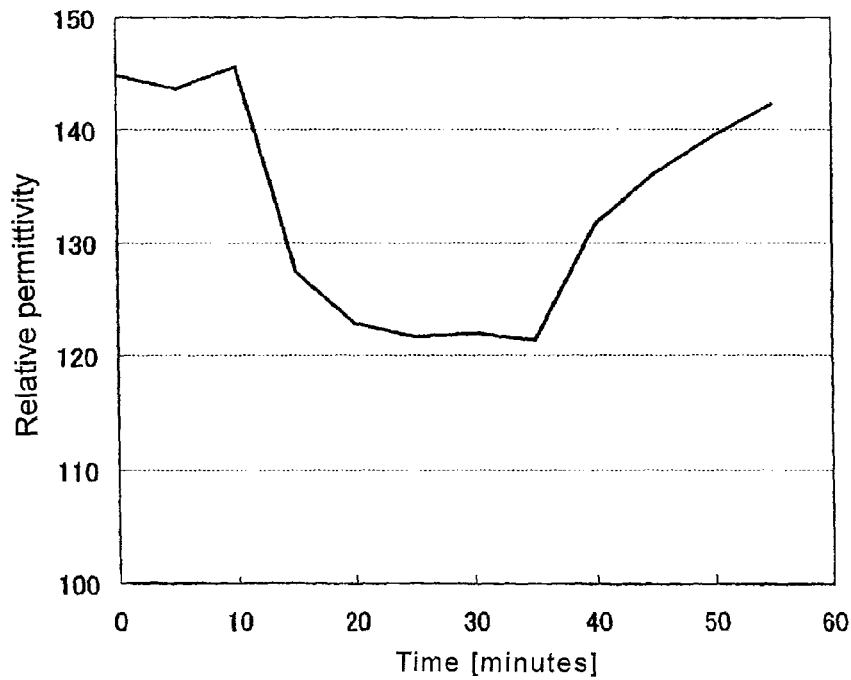
FIG. 14 is a graph showing the result of measuring water at 250 degrees C. by the gas sensor according to Example 1-2.

A gas sensor was prepared by a manufacturing process which was the same as the process described in Example 1-1. The gas sensor was subjected to a heating treatment in a vacuum atmosphere as the start-up process. The gas sensor was disposed in the chamber, the pure nitrogen gas was introduced into the chamber, and the measurement of the relative permittivity was started. After starting the measurement, the line introducing the gas into the chamber was switched to a blended gas having a total pressure of 1 atm at 1 L/minute. The blended gas consisted of the pure nitrogen gas and water, with the water being blended so that the water content of the blended gas was 10 ppm. The blended gas will be referred to as nitrogen gas containing 10 ppm of water. As shown in FIG. 14, a sharp decline in the relative permittivity (from 145 to 127) was observed. This tendency was similar to the tendency observed in Example 1-1.

Fifteen minutes after introducing the nitrogen gas containing 10 ppm of water, the decrease of the measured relative permittivity was saturated and the relative permittivity was almost stabilized at 120. Twenty-five minutes after introducing the nitrogen gas containing 10 ppm of water, the gas line was switched to the line for introducing the pure nitrogen gas. The relative permittivity then rapidly increased, and twenty minutes after introducing the pure nitrogen gas, the relative permittivity recovered to a level similar to the relative permittivity before introducing the nitrogen gas containing 10 ppm of water.

(3) Example 1-3

An experiment similar to the experiment in Example 1-2 was performed. In this experiment, the temperature of the gas sensor during the measurement was maintained at 150 degrees C.

Figure 15:
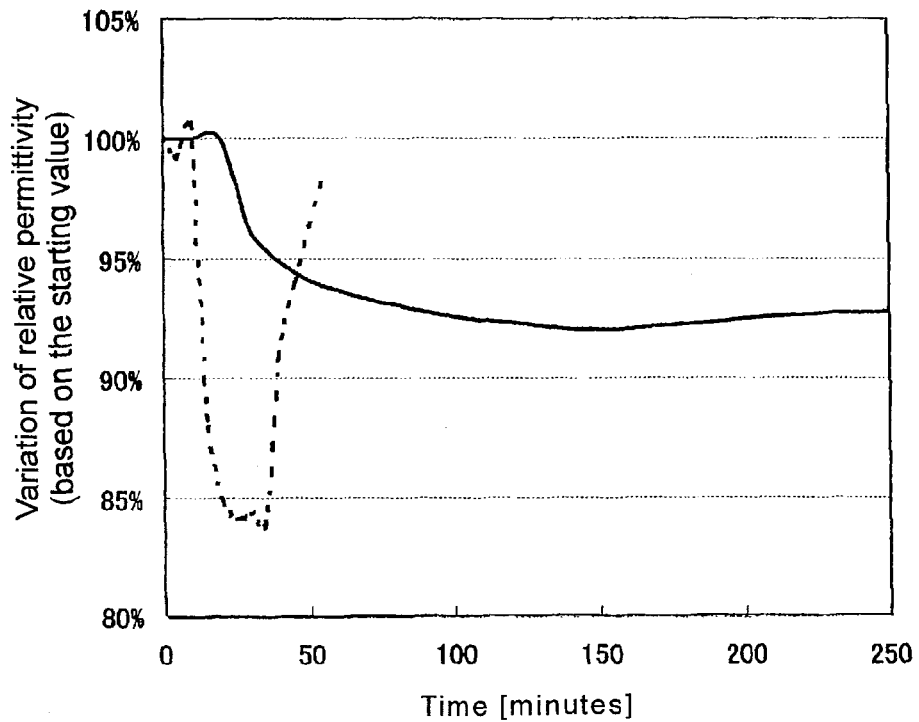
FIG. 15 is a graph showing the result of measuring water at 150 degrees C. by the gas sensor according to Example 1-3.

The result is shown in FIG. 15. In this figure, the measured relative permittivity was normalized by the initial value before introducing the nitrogen gas containing 10 ppm of water for ease of comparison with the result when the temperature of the gas sensor was maintained at 250 degrees C. The result obtained at 150 degrees C. is shown by the solid line in FIG. 15, and the result obtained at 250 degrees C. is shown by the dashed line in this figure. As shown in FIG. 15, the basic tendency of the result at 150 degrees C. consists of a decrease with time in the relative permittivity and a decrease over time with the moderate rate of decrease of the relative permittivity. This tendency was similar to the tendency of the result of Example 1-2. However, the relative permittivity was saturated at almost 92% of its initial value, and the period until the saturation was reached was prolonged by almost two hours. In comparison with the result at 250 degrees C., the relative permittivity at 150 degrees C. decreased by one-half, and the length of time until saturation was reached was eight times as long.

One hundred thirty minutes after introducing the nitrogen gas containing 10 ppm of water, the gas line was switched for the line of the pure nitrogen gas. The relative permittivity then increased more slowly in comparison to the case of Example 1-2, and even one hundred minutes after introducing the pure nitrogen gas, the relative permittivity recovered to about only 93% of the initial value. However, the relative permittivity could be restored to the initial value by heating at 300 degrees C. for one hour.

(4) Example 1-4

A glass substrate having an area of 30 mm×30 mm and a thickness of 0.12 to 0.17 mm was prepared. The substrate was placed in a vacuum chamber containing atmosphere at $1\times10^{-5}$ Pa with the content of residual oxygen of at most 10 ppb, namely, at most $10^{11}$ molecules/cm$^3$. Then, a rectangular pattern (20 mm×4 mm) as a lower electrode and a pattern contacting the rectangular pattern and having the shape of a line as a drain electrode were formed by depositing aluminum. The thickness of these patterns was almost 100 nm.

A boat made of molybdenum and filled with a $C_{60}$ fullerene mixture containing 5% by weight of endohedral lithium $C_{60}$ fullerene (sold as 001A by Ideal Star, Inc.) was heated in the chamber. The temperature of the molybdenum boat was measured during heating and was controlled to be in the range of 550 to 600 degrees C. so as to sublimate the fullerene mixture containing lithium endohedral $C_{60}$ fullerene. A film of the $C_{60}$ fullerene mixture having a thickness of 2 micrometers was formed by the sublimation on the above-described pattern of aluminum forming the lower electrode. The $C_{60}$ fullerene mixture film had the shape of a rectangle so as to completely cover the underlying aluminum pattern.

A pattern of aluminum having the identical shape as the aluminum pattern forming the lower electrode was deposited on the $C_{60}$ fullerene mixture film. The aluminum pattern had a thickness of 200 nm. A drain electrode for this electrode was also formed by depositing aluminum so as not to overlap the drain electrode for the lower electrode.

This layered structure formed by the above-described process was subjected to an air-exposure process and a start-up process by heating at 280 degrees C. for 6 hours as in Example 1-1. The temperature of the gas sensor was maintained at 250 degrees C., the pure nitrogen gas was introduced at 1 L/min into the measurement chamber, and measurement of the relative permittivity was started.

Figure 16:
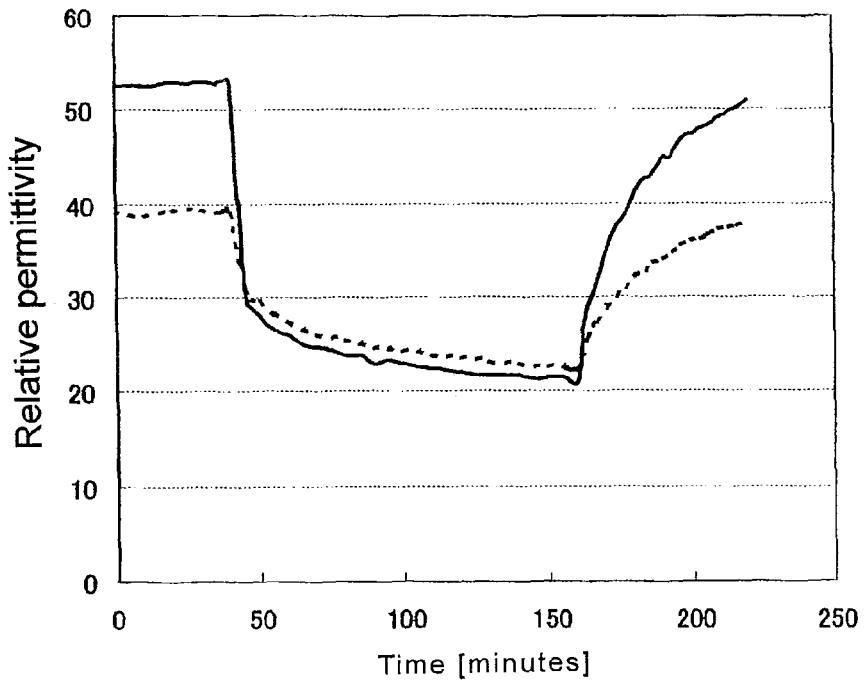
FIG. 16 is a graph showing the result of measuring oxygen at 250 degrees C. by the gas sensor according to Example 1-4.

After confirming that the measurement environment was stabilized because the relative permittivity was stabilized at 52, the introduction of the nitrogen gas containing 1 ppm of oxygen was started as in Example 1-1. As shown in FIG. 16, a sharp decline of the relative permittivity (from 40 to 30) was observed and the relative permittivity decreased to 30 five minutes later after the introduction. Subsequently, while the rate of decrease fell over time, the relative permittivity decreased to 20 at one hundred twenty minutes after introducing the nitrogen gas containing 1 ppm of oxygen.

The above-described result was compared with the result of the gas sensor having a gas detection device consisting only of $C_{60}$ fullerene, which is shown by a dashed line in FIG. 16 as a reference result. While the initial value of the relative permittivity obtained in the present result was larger that the initial value obtained in the reference result, both values of the relative permittivity likewise decreased to 20 when oxygen was adsorbed. Therefore, it was confirmed by the above-described examples that the sensitivity of the gas sensor increased by adding lithium endohedral $C_{60}$ fullerene in the gas detection device of the gas sensor.

Afterward, the pure nitrogen gas was introduced into the chamber by switching the gas line. Then, the relative permittivity rapidly increased and recovered to a level similar to the initial value at 1 hour later after switching the gas line. Here, the electric power applied to the carbon heater increased so that the temperature at the surface of the gas sensor reached 280 degrees C., and then, the relative permittivity recovered to the initial value at 1 hour later after heating the surface of the gas sensor at 280 degrees C.

(5) Comparative Example 1

A glass substrate having an area of 30 mm×30 mm and a thickness of 0.12 to 0.17 mm was prepared. The substrate was placed in a vacuum chamber containing an atmosphere at $1\times10^{-5}$ Pa with the content of residual oxygen of at most 10 ppb, namely, at most $10^{11}$ molecules/cm$^3$. Then, two rectangular patterns (20 mm×2 mm) were formed as lower electrodes by depositing gold so that the gap between these electrodes was 2 mm. Two line-shaped patterns were formed as drain electrodes by depositing gold so as to respectively contact the lower electrodes. The thickness of these gold patterns was almost 100 nm.

A boat made of molybdenum and filled with $C_{60}$ fullerene (Nanom Purple of Frontier Carbon Co. Ltd) was heated in the chamber. The temperature of the molybdenum boat was measured during heating and was maintained in the range of 500 to 550 degrees C. so as to sublimate $C_{60}$ fullerene. A film of $C_{60}$ fullerene having a thickness of 2 micrometers was formed by the sublimation on the above-described gold patterns forming lower electrodes and on the gap between these electrodes.

The pressure in the chamber was maintained at $1\times10^{-5}$ Pa, and the content of residual oxygen was at most 0.1 ppb. The gas sensor in the chamber was subjected to a start-up process by heating at 280 degrees C. at 6 hours as in Example 1-1.

After the start-up process, the carbon heater was adjusted so that the temperature at the surface of the gas sensor was maintained at 250 degrees C. Connectors from the impedance analyzer were connected to the electrodes, a DC voltage of 20 V was applied to the electrodes, and measurement of the specific resistance of the gas sensor was started.

Figure 17:
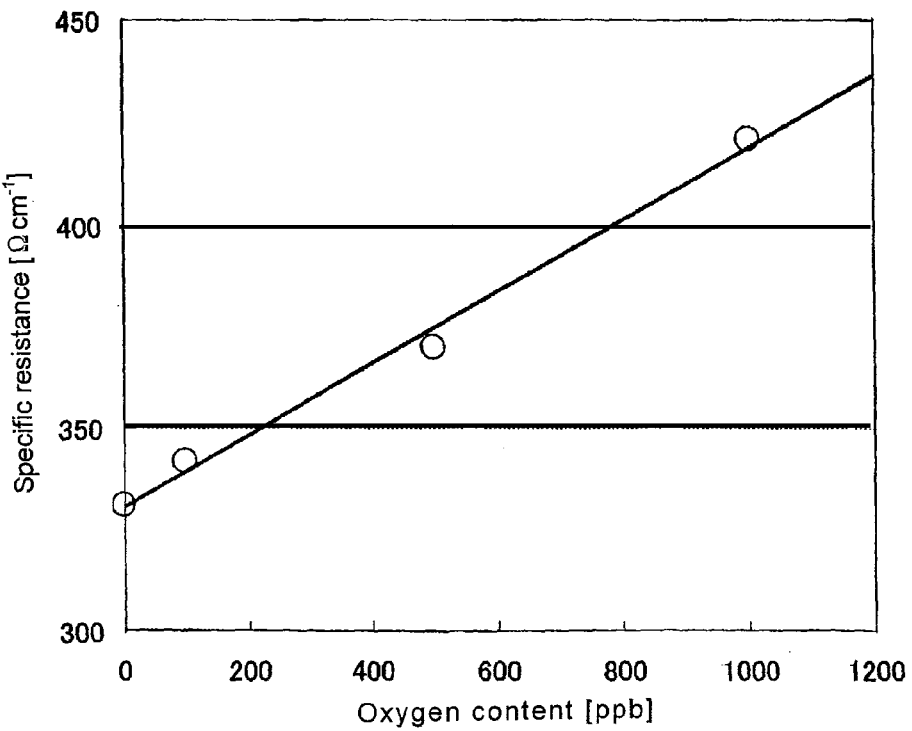
FIG. 17 is a graph showing the result of measuring oxygen at 250 degrees C. by the gas sensor according to Comparative example 1.

After the measurement of the specific resistance in pure nitrogen gas, oxygen was added to the introduced pure nitrogen gas and the oxygen content in the chamber was increased in a stepwise fashion. The specific resistance was measured at each step when the variation of the specific resistance was stabilized after changing the oxygen content. As a result, the dependency of the specific resistance on the oxygen content was obtained, as shown in FIG. 17, in which measured data are shown by circles and fitted data are shown by a solid line.

As shown in this figure, the gas sensor exhibited good linearity. Therefore it was confirmed that the gas sensor had sufficient basic properties required of a gas sensor. However, it took almost two hours until the specific resistance was stabilized after changing the oxygen content. In addition, after the specific resistance of the gas sensor was measured in an atmosphere containing 1000 ppb of oxygen, it took over 20 hours until the specific resistance recovered to the initial value after the gas sensor was heated to 280 degrees C.

Although a similar measurement was performed in an atmosphere containing water, a variation of the resistance as was measured in an atmosphere containing oxygen was not observed.

EXAMPLE 2

Different compositions of the gas sensor according to the present invention, especially compositions in which the configuration of the capacitive element is different from that in Example 1, will be explained in this example.

As described above, the gas detection device consisting of a $C_{60}$ fullerene deposited film has the characteristics that the electric conductivity of the gas detection device decreases as the amount of gases adsorbed in the gas detection device increases. Similarly, the gas detection device consisting of a $C_{60}$ fullerene deposited film has the characteristics that the electric conductivity of the gas detection device decreases as the temperature of the gas detection device decreases.

In Example 2, gas sensors having different configurations of capacitive elements were prepared, and the function of each gas sensor was investigated by varying the temperature of the gas detection device instead of by varying the amount of gases adsorbed to the gas detection device.

(1) Example 2-1

A glass substrate having an area of 30 mm×30 mm and a thickness of 0.12 to 0.17 mm was prepared. The surface of the substrate was previously polished so as to have a surface roughness Ra of at most 20 nm. The substrate also had two patterns of gold deposited film as pad electrodes at prescribed locations on the polished surface. The substrate was placed in a vacuum chamber evacuated at the pressure of $3 \times 10^{-5}$ Pa for depositing aluminum. Then, a rectangular pattern (4 mm×6 mm) was formed as a lower electrode, and a linear pattern contacting the rectangular pattern was formed as a drain electrode, both of which were formed by depositing aluminum. The rate of deposition was 1.5 angstroms per second, and the thickness of the patterns was almost 50 nm. The linear pattern was electrically connected with one of the gold pad electrodes.

The substrate on which aluminum was deposited was then placed into a vacuum chamber with a high vacuum at the pressure of $1 \times 10^{-4}$ Pa for depositing fullerenes, where the residual oxygen content was at most 1 ppb. An air-exposure period between opening the chamber for depositing aluminum and placing the substrate into the chamber for fullerenes was at most 20 minutes. A boat made of molybdenum and filled with $C_{60}$ fullerene, (Nanom Purple, which is a product of Frontier Carbon Co. Ltd.) was heated in the chamber. The temperature of the molybdenum boat was measured during heating and was controlled to be in the range of 500 to 550 degrees C. so as to sublimate $C_{60}$ fullerene at 3 to 4 angstrom per second. A film of $C_{60}$ fullerene having a thickness of 1.4 micrometers was formed by the sublimation on the above-described aluminum pattern forming the lower electrode. The $C_{60}$ fullerene film had the shape of a rectangle so as to completely cover the underlying aluminum pattern.

The substrate having the $C_{60}$ fullerene film was again placed into the above-described chamber for depositing aluminum. The air-exposure period this time was at most 20 minutes.

A pattern of aluminum having a narrower shape (2 mm×5 mm) than the aluminum pattern of the lower electrode was deposited on the $C_{60}$ fullerene film. The deposition rate was the same as the above-described rate of depositing aluminum, and the aluminum pattern also had a thickness of 50 nm. A drain electrode for this electrode was also formed by depositing aluminum so as not to overlap the drain electrode for the lower electrode but so as to partly overlap the other of the gold pad electrodes.

The substrate was then taken out from the chamber and subjected to an air-exposure process comprising exposure to the ambient air (25 degrees C. and 60% RH) for 24 hours so as to form oxide films on the interfaces of the deposited aluminum films. The capacitance of the capacitive element containing the oxide films was about 15 nF. In this way, a gas sensor having an effective electrode area of 10 mm$^2$ was obtained.

This gas sensor was placed in a measurement chamber. The atmosphere of the chamber was maintained at 10 Pa. A carbon heater was attached to the surface of the glass substrate of the gas sensor opposite to the surface on which deposited layers were formed. The carbon heater was heated for 24 hours at 220±10 degrees C. measured at the surface of the gas sensor to perform a start-up process.

After the start-up process, the carbon heater was adjusted so that the temperature at the surface of the gas sensor was maintained at 200 degrees C. Then, connectors from a power supply capable of applying an AC voltage having an arbitrary frequency from 0.01 Hz to 10 MHz were respectively connected with the two drain electrodes.

An AC voltage of 50 mV was applied to the electrodes while varying the frequency of the applied voltage from 0.01 Hz to 10 MHz, and the variation of the impedance of the gas sensor was measured. The variation of the capacitance was calculated based on the measured variation of the impedance, and the capacitance profile at 200 degrees C. was obtained from the variation of the impedance.

Next, the temperature of the surface of the gas sensor was decreased to 180 degrees C. by controlling the temperature of the carbon heater. After confirming that the temperature was maintained at the fixed temperature, the variation of the impedance of the gas sensor was measured by varying the frequency of the applied AC voltage and the capacitance profile was obtained. In the same manner, the surface temperature of the gas sensor was decreased to 25 degrees C. in a stepwise fashion and the capacitance profile was measured at each temperature.

Figure 18:
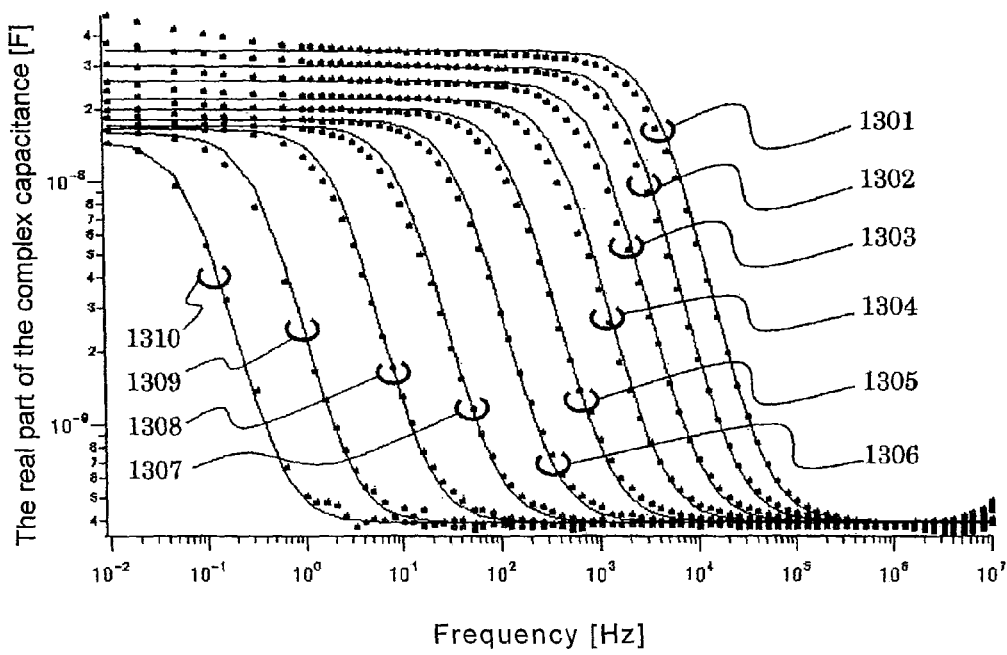
FIG. 18 is a graph showing the capacitance profiles at different temperatures (shown by circles) obtained from the gas sensor according to Example 2-1 and the fitted results (shown by lines) of the capacitance profiles.

Results of the above-described measurements are shown in FIG. 18. The dots in FIG. 18 indicate the measured values, and the solid lines indicate the fitted results based on the equivalent circuit shown in FIG. 6. The profile indicated by reference number 1301 shows the result measured at 200 degrees C., and the profiles indicated by reference numbers 1302 to 1310 show the results at 180 degrees C., 160 degrees C., 140 degrees C., 120 degrees C., 100 degrees C., 80 degrees C., 60 degrees C., 40 degrees C., and 25 degrees C., respectively.

As shown in FIG. 18, the capacitance profile at any temperature had a shape such that the capacitance was low in the high-frequency zone, the capacitance was high in the low-frequency zone, and there was a transition zone having a width of frequency $10^3$ Hz between the above two zones. The transition zone shifted in the direction of a higher frequency as the temperature of the gas sensor increased, and the electric conductivity of the gas detection device therefore increased. The center frequency of the transition zone was at 10 kHz when the temperature of the gas sensor was 200 degrees C. On the other hand, when the temperature of the gas sensor was 25 degrees C., the center frequency of the transition zone was at 0.2 Hz because of a decrease in the electric conductivity of the gas sensor. These results indicate that the variation of the electric conductivity of the gas detection device is measurable as a change of the shape of the capacitance profile. The measured values were fitted by assuming that the equivalent circuit of the gas sensor according to the present invention was the circuit shown in FIG. 6. According to the fitted results, the electric conductivity of the gas detection device was estimated to vary from about $10^{-11}$ (ohm cm)$^{-1}$ to about $10^{-6}$ (ohm cm)$^{-1}$.

Accordingly, it is shown by this example that the amount of gases adsorbed by the gas detection device can be estimated from the capacitance profile, because a change in electric conductivity similar to the above-described change occurs when gases are adsorbed by the gas detection device.

As an overall trend, the capacitance of the low-frequency zone was found to be higher as the temperature increased. It is thought based on a simulation that the trend was mainly caused by varying the resistances between the $C_{60}$ fullerene film and the aluminum layers in accordance with the variation of the temperature of the gas sensor.

In addition, a trend for the capacitance to gradually increase as the frequency decreased in a low-frequency zone was observed in the measured capacitance profiles. It is thought that this trend was caused by varying the resistance of the resistive component contained in the capacitive element in accordance with the variation of the temperature of the gas sensor.

(2) Example 2-2

A gas sensor was prepared by the manufacturing process described in Example 2-1 except that the deposited material for electrodes was changed from aluminum to gold. The start-up process described in Example 2-1 was performed for the produced gas sensor. After the start-up process, the surface temperature of the gas sensor was maintained at 200 degrees C. Connectors from a power supply which can apply an AC voltage having a frequency from 0.01 Hz to 10 MHz were then connected with the two drain electrodes.

An AC voltage of 50 mV was applied to the electrodes while frequency of the applied voltage was swept from 0.01 Hz to 10 MHz, and the variation of the impedance of the gas sensor was measured. The capacitance was calculated based on the measured impedance, and the capacitance profile at 200 degrees C. was obtained. The surface temperature of the gas sensor was decreased in a stepwise fashion, and the capacitance profile was measured at each temperature as in Example 2-1.

Figure 19:
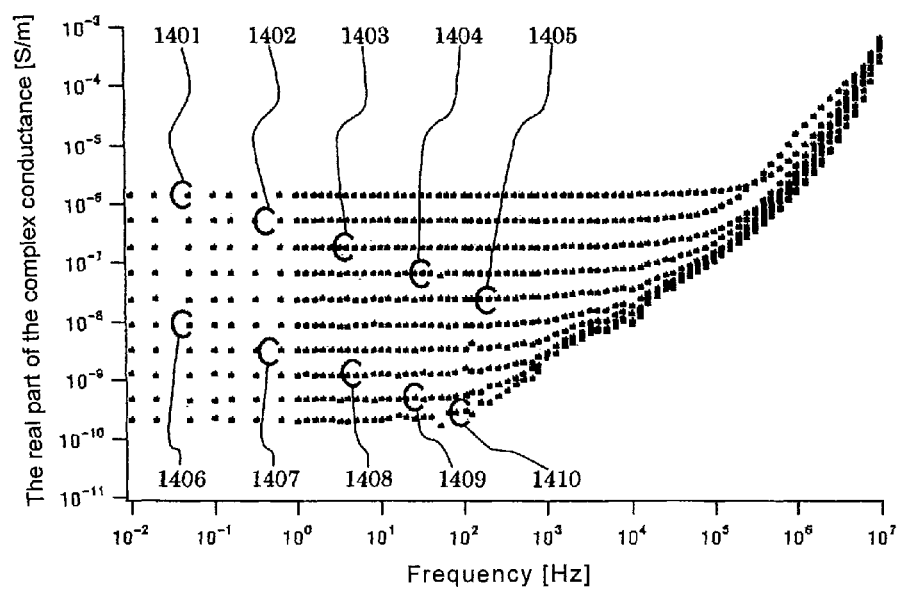
FIG. 19 is a graph showing the conductance profiles at different temperatures obtained from the gas sensor according to Example 2-2.

The results of the above-described measurements are shown in FIG. 19. The profile indicated by reference number 1401 shows the result measured at 200 degrees C., and the profiles indicated by reference numbers 1402 to 1410 show the results at 180 degrees C., 160 degrees C., 140 degrees C., 120 degrees C., 100 degrees C., 80 degrees C., 60 degrees C., 40 degrees C., and 24 degrees C., respectively.

As shown in FIG. 19, the capacitance profile at any temperature had a tendency for the capacitance to be flat in the low-frequency zone and for the capacitance to increase as the frequency became higher in the high-frequency zone. The threshold frequency where the trend of the capacitance changed from flat to increasing became higher as the temperature increased, namely, a gas detection device decreased in electric conductivity.

(3) Example 2-3

A gas sensor was prepared by the manufacturing process described in Example 2-2. The start-up process described in Example 2-2 was performed for the produced gas sensor. After the start-up process, the surface temperature of the gas sensor was maintained at 210 degrees C. Connectors from a power supply which can apply an AC voltage having a frequency from 5 Hz to 5 MHz were then connected with the two drain electrodes. An AC voltage of 50 mV was applied to the electrodes while frequency of the applied voltage was swept from 50 Hz to 5 MHz, and the impedance of the gas sensor was measured. The capacitance was calculated based on the measured impedance and the capacitance profile at 210 degrees C. was obtained. The result is shown by solid circles in FIG. 20.

A commercially available capacitor having a capacitance of 1 nF (1000 pF) was then placed between one of the drain electrodes and the power supply. The surface temperature of the gas sensor was maintained at 210 degrees C., and the capacitance profile was measured. The result is shown by triangles in FIG. 20.

The 1 nF capacitor was then replaced by a commercially available 10 nF (10000 pF) capacitor. The surface temperature of the gas sensor was maintained at 210 degrees C., and the capacitance profile was measured. The result is shown by diamonds in FIG. 20.

Figure 20:
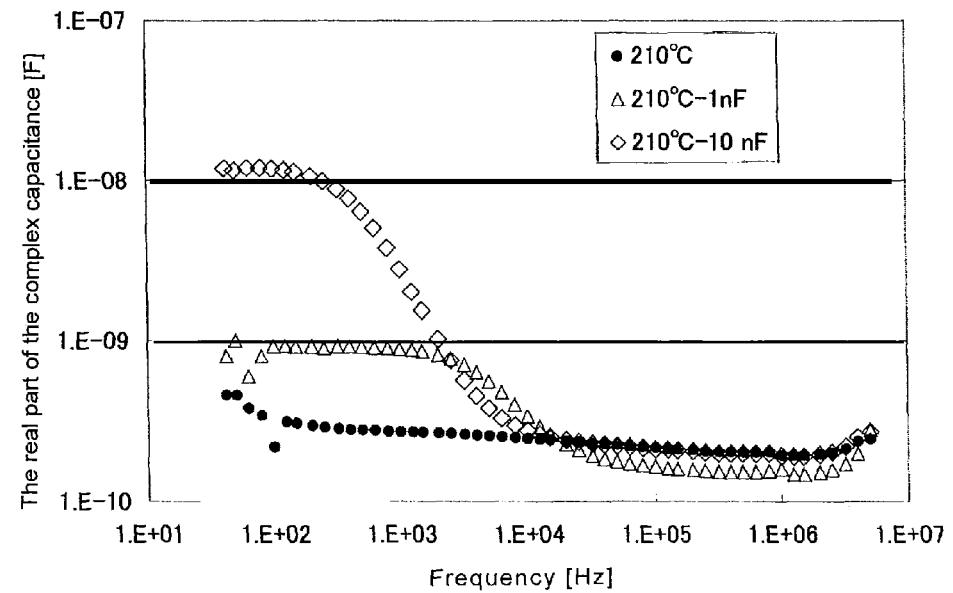
FIG. 20 is a graph showing the capacitance profiles obtained from the gas sensor according to Example 2-2, from a gas sensor in which an external capacitor having a capacitance of 1 nF is connected to the gas sensor according to Example 2-2, and from a gas sensor in which an external capacitor having a capacitance of 10 nF is connected to the gas sensor according to Example 2-2.

As shown in FIG. 20, the shape of the capacitance profile was flat when a capacitor was not interposed. However, when a 1 nF capacitor was interposed, the capacitance was increased in the low-frequency zone and the transition zone was observed between 2 kHz to 50 KHz. When a 10 nF capacitor was interposed, the capacitance in the low-frequency zone became higher, and the transition zone was observed between 2 kHz to 50 KHz.

These results indicate that the capacitance profile can be measured even from an electric element having a simple structure consisting of a gas detection device and electrodes which are disposed at both electric terminals of the gas detection device and formed from inert metal layers when an external capacitor is installed. These results also indicate that the shape of the capacitance profile can be modified by installing an external capacitor.

The invention claimed is:

1. A gas sensor comprising:
   a gas detection device containing a dielectric semiconductor, the electric conductivity of the gas detection device varying in response to the degree of adsorption of gases to the gas detection device;
   a capacitive element connected in series to the gas detection device, the capacitance of the capacitive element being larger than the capacitance of the gas detection device; and
   a pair of electrodes which are connected to electric terminals of an electric element comprising the gas detection device and the capacitive element,
   wherein the gas sensor is capable of detecting the degree of adsorption of gases to the gas detection device from an electrical response changing in response to a voltage which is applied to the pair of electrodes and which periodically varies and reverses in polarity,
   wherein the gas sensor comprises a pair of inert metal layers each formed directly on the surface of one of the electric terminals of the gas detection device, and
   wherein the gas detection device and the pair of inert metal layers sandwiching the gas detection device forms a gas detection module which does not substantially contain an electric element which has dielectric characteristics other than the gas detection device.

2. The gas sensor according to claim 1, wherein the gas sensor is composed of the gas detection module and a capacitor as the capacitive element which is connected in series to the gas detection module.

3. The gas sensor according to claim 1, wherein the dielectric semiconductor comprises a fullerene material having electric conductivity which is decreased by the adsorption of a gas.

4. The gas sensor according to claim 1, wherein the dielectric semiconductor comprises an organic semiconductor.

5. The gas sensor according to claim 1, wherein the dielectric semiconductor comprises a carbon nanomaterial.

6. A gas measuring system comprising:
   a gas sensor according to claim 1,
   an electric power supply capable of applying a voltage to the electric terminals of the gas sensor, wherein the applied voltage periodically varies and reverses in polarity, and
   a measuring means for measuring an electric response of the gas sensor to the voltage applied by the electric power supply.

7. The gas measuring system according to claim 6, further comprising a gas desorbing means for desorbing a gas adsorbed by the dielectric semiconductor contained in the gas sensor.

8. The gas measuring system according to claim 6 further comprising a temperature measuring means for measuring the temperature of the gas sensor, wherein the structure of the temperature measuring means is the same as that of the gas sensor except that the temperature measuring means is sealed so that no gas is adsorbed by a gas detection device of the temperature measuring means.

9. A gas detection module for a gas measuring system comprising a gas detection device according to claim 1 and a pair of inert metal layers respectively formed directly on the surface of electric terminals of the gas detection device, wherein the gas detection module does not substantially contain an electric element which has dielectric characteristics other than the gas detection device.

10. A method of measuring gases using a gas measuring system, the method comprising:

providing a gas sensor according to claim 1;
applying a voltage from an electric power supply to electric terminals of the gas sensor, the applied voltage periodically varying and reversing in polarity; and
measuring an electric response of the gas sensor to the voltage applied by the electric power supply,
wherein the dependence of the real part of the complex capacitance of the gas sensor on the frequency of the applied voltage has a profile which consists of a first zone at a higher frequency, a second zone at a lower frequency, and a third zone between the first zone and the second zone, a value of the first zone being defined mainly by the capacitance of the gas detection device of the gas sensor, and a value of the second zone being defined mainly by the capacitance of the gas detection device; and
the degree of adsorption of gases to the gas sensor is detected by measuring at least one of the value of the second zone and a value of the third zone of the profile.

* * * * *

UNITED STATES PATENT AND TRADEMARK OFFICE
CERTIFICATE OF CORRECTION

PATENT NO.       : 8,381,587 B2                                                                 Page 1 of 1
APPLICATION NO.  : 12/599268
DATED            : February 26, 2013
INVENTOR(S)      : Kasama et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 638 days.

Signed and Sealed this
First Day of September, 2015

Michelle K. Lee
*Director of the United States Patent and Trademark Office*